(12) United States Patent
Muise et al.

(10) Patent No.: US 12,220,561 B2
(45) Date of Patent: Feb. 11, 2025

(54) SHIELD ASSEMBLY FOR SYRINGE

(71) Applicant: Cheryl Muise, London (CA)

(72) Inventors: Cheryl Muise, London (CA); Nicholas Teixeira, Angus (CA); Steve A. Copeland, Barrie (CA)

(73) Assignee: Cheryl Muise, London (CA)

( * ) Notice: Subject to any disclaimer, the term of this patent is extended or adjusted under 35 U.S.C. 154(b) by 350 days.

(21) Appl. No.: 17/568,003

(22) Filed: Jan. 4, 2022

(65) Prior Publication Data

US 2022/0218908 A1   Jul. 14, 2022

Related U.S. Application Data

(60) Provisional application No. 63/137,372, filed on Jan. 14, 2021.

(51) Int. Cl.
| | | |
|---|---|---|
| *A61M 5/31* | (2006.01) | |
| *A61M 5/32* | (2006.01) | |
| *A61M 5/42* | (2006.01) | |

(52) U.S. Cl.
CPC ........ *A61M 5/3134* (2013.01); *A61M 5/3202* (2013.01); *A61M 5/3243* (2013.01); *A61M 5/427* (2013.01); *A61M 2205/59* (2013.01)

(58) Field of Classification Search
CPC .. A61M 5/3134; A61M 5/3202; A61M 5/427; A61M 5/3243; A61M 2205/59
See application file for complete search history.

(56) References Cited

U.S. PATENT DOCUMENTS

| | | | |
|---|---|---|---|
| 2008/0139076 A1* | 6/2008 | Frasier-Scott | .......... A61M 5/14 446/72 |
| 2019/0030444 A1* | 1/2019 | Corwin | ..................... F16B 2/22 |

* cited by examiner

*Primary Examiner* — Tasnim Mehjabin Ahmed
(74) *Attorney, Agent, or Firm* — Sand, Sebolt & Wernow Co., LPA

(57) ABSTRACT

A shield assembly for a syringe includes a cradle, a carriage, and a shield. The cradle is configured to be operatively engaged around a portion of a circumference of a syringe barrel. The shield is configured to extend longitudinally outwardly from the cradle to cover a needle of the syringe. The carriage secures the shield to the cradle and is configured to be movably engaged with the cradle. The shield is detachably engaged with the carriage and is configured to be aesthetically pleasing to a young child. The shield assembly is engaged with the syringe prior to use so as to reduce stress in the young child while they are either being injected with a substance or having their blood drawn. After the procedure, the shield may be detached from the shield assembly and may be given to the young patient.

11 Claims, 27 Drawing Sheets

SHIELD ASSEMBLY FOR SYRINGE

CROSS-REFERENCE TO RELATED APPLICATIONS

This application claims the benefit of U.S. Provisional Patent Application Ser. No. 63/137,372, filed Jan. 14, 2021, the entire disclosure of which is incorporated herein by reference.

BACKGROUND

Technical Field

This disclosure is directed to medical devices. More particularly, the disclosure is directed to syringes which are used to inject a volume of a medicine or a vaccine into a patient's body via a hollow needle or to withdraw blood or other fluids from the patient's body through the needle. Specifically, the disclosure relates to a shield assembly that is removably operatively engaged with a syringe barrel. The shield assembly includes a shield which prevents a patient, particularly a young child, from seeing the needle which extends outwardly from the syringe.

Background Information

Syringes are used in a variety of different activities relating to medical treatment. They may, for instance, be used to deliver a dose of medicine to a patient that is ill or needs periodic administration of a medicine to control a medical condition. In preventative medicine syringes may be used to vaccinate or inoculate a person by delivering a dose of vaccine into their body. The dose of vaccine is specific to a particular disease, such as infectious disease, and, once delivered, the vaccine will hopefully produce an immune response in the person's body. If the person is later exposed to that disease, the developed immunity may aid the person in fighting the disease and thereby may prevent illness or at least decrease the severity of illness from that disease. Currently, countries all over the world are vaccinating their populations against COVID-19 and these vaccinations are being administered using syringes.

Syringes deliver the dose of medicine or vaccine through a hollow needle. The tip of the needle is used to puncture the person's skin and is moved to the correct location to deliver the medicine or vaccine. In some instances, the liquid is to be introduced into the fat layer between the skin and muscle. This type of injection is known as a subcutaneous injection. In other instances, the liquid medicine or vaccine is to be delivered into a muscle. This type of injection is referred to as an intramuscular injection. In yet other instances, the liquid is to be introduced into a person's vein. In this instance, the injection is referred to as an intravenous injection.

In yet other instances, blood is withdrawn from a person's veins or other liquids are withdrawn from a person's body using a syringe. Whether delivering a medicine or vaccine or withdrawing some type of fluid from the body, a needle is required on the syringe. This makes the procedure that is undertaken painful and many people are quite fearful of having medicine or vaccine delivered via injection or blood or other fluid withdrawn via a syringe. While older children and adults will cooperate to a greater or lesser degree during such procedures, young children can become extremely fearful if they have previously had an encounter with a syringe. They may therefore become quite distressed and uncooperative, making the administering of medicine or vaccine, or the withdrawal of blood or fluid extremely challenging.

The prior art discloses a number of solutions to address this problem. For example, Smeton (U.S. Pat. No. 3,299,891) discloses an attachment member in a 3-D shape of an animal that will be aesthetically pleasing to a young child. The attachment member includes a cylindrical bore into which the barrel of a syringe is inserted in such a way that the barrel and hub of the syringe are entirely enclosed by the attachment member and the needle on the syringe extends outwardly from a front end of the attachment member.

U.S. Publication 2012/0061286 (Hueb De Menezes Oliveira et al) discloses a sleeve for a syringe that is shaped to be pleasing to a child. The sleeve completely surrounds the syringe barrel and is disclosed to additionally cover the needle. The device includes a bellow or bulb section to retract the sleeve in order to project the needle from a front end thereof.

GB2336541 (Ross), discloses a sheath that is configured to be pleasing to a young child. The sheath has a bore for receiving a syringe therein such that a needle on the syringe is able to project forwardly and outwardly from the sheath through an aperture at one end thereof.

Japanese Patent No. JP3613788 (Publication No. JP2001190576) issued to Sakamata Kazuo discloses a cover body that is detachably attached to the syringe and which is shaped as a toy that would be aesthetically pleasing to a child. The cover body completely surrounds the syringe barrel and the needle extends outwardly from an end of the cover body.

JP20023275307 (Kaneda Toshio) discloses a tubular decorative cover for a barrel of a syringe that includes pleasing images thereon. The cover is slipped over the barrel of the syringe so that the hub and needle of the syringe extend outwardly from one end of the cover.

KR100834541 (Ahn Jun Seo) discloses a sheath for a syringe that is slipped onto a front end of a syringe barrel such that an end portion of the barrel, the hub, and part of the needle may be obscured but most of the syringe is still visible to the patient. The sheath is configured to be pleasing to a young child.

SUMMARY

The device disclosed herein is designed to reduce the fear a younger child may experience in medical settings where medicine or vaccine is to be administered via a syringe or if blood or another body fluid is to be drawn via a syringe.

The disclosed device comprises a shield assembly for a syringe that includes a cradle, a carriage, and a shield. The cradle is configured to be operatively engaged around a portion of a circumference of a syringe barrel. The shield is configured to extend longitudinally outwardly from the cradle to cover a needle of the syringe. The carriage secures the shield to the cradle and is configured to be movably engaged with the cradle. The shield is detachably engaged with the carriage and is configured to be aesthetically pleasing to a young child. The shield assembly is engaged with the syringe prior to use so as to reduce stress in the young child while they are either being injected with a substance or having their blood drawn. After the procedure, the shield may be detached from the shield assembly and may be given to the young patient.

In one aspect, an exemplary embodiment of the present disclosure may provide a shield assembly for a syringe comprising a cradle configured to operatively engage a portion of the syringe; and a shield operatively engaged with the cradle, said shield being adapted to cover a needle extending outwardly from a barrel of the syringe.

In one embodiment, the shield assembly may further comprise a carriage operative to engage the shield to the cradle. In one embodiment, the carriage may be movably engaged with the cradle. In one embodiment, the shield assembly may further comprise a slot defined in the cradle; a projection provided on the carriage, said projection sized to be received through the slot; wherein the projection and thereby the carriage are selectively slidable along the slot. In one embodiment, the shield may be detachably engaged with the carriage. In one embodiment, the shield may be snap-fittingly engaged with the carriage.

In one embodiment, the shield assembly may further comprise an aesthetically pleasing image provided on the shield. In one embodiment, the aesthetically pleasing image on the shield may comprise a sticker applied to the shield. In one embodiment, the shield may be three-dimensionally formed into the aesthetically pleasing image. In one embodiment the cradle may be adapted to extend around a portion of a circumference of the barrel of the syringe. In one embodiment, the shield assembly may further comprise one or more spring clips provided on the cradle, said one or more spring clips being adapted to engage a portion of a circumference of the barrel of the syringe. In one embodiment, the shield assembly may further comprise a rounded bottom edge provided on the shield, wherein the rounded bottom edge is adapted to contact skin of a patient during use of the syringe.

In another aspect, an exemplary embodiment of the present disclosure may provide a method of reducing stress in a patient receiving medical treatment comprising engaging a cradle of a shield assembly with a syringe; extending a shield of the shield assembly over a needle extending outwardly from a barrel of the syringe; placing an edge of the shield against the patient's skin; piercing the patient's skin with a tip of the needle; manipulating a plunger extending from the syringe's barrel to perform one of injecting a substance into the patient's body and withdrawing fluid from the patient's body; and withdrawing the needle from the patient's skin.

In one embodiment, the method may further comprise hiding the needle from the patient's view with the shield prior to piercing the patient's skin up to after withdrawing the needle from the patient's skin. In one embodiment the method may further comprise providing a child-pleasing image on the shield. In one embodiment, providing the child-pleasing image on the shield may include providing a sticker on a front face of the shield. In one embodiment, engaging the cradle with the syringe may include snap-fitting one or more spring clips provided on the cradle around a portion of a circumference of a barrel of the syringe. In one embodiment, engaging the shield with the cradle may include engaging a movable carriage with the cradle and mounting the shield on the movable carriage. In one embodiment, the method may further comprise defining a slot in the cradle; extending a projection on the carriage through the slot defined in the cradle; and sliding the projection and thereby the carriage along the slot. In one embodiment, the method may further comprise detachably engaging the shield with the cradle.

In another aspect, an exemplary embodiment of the present disclosure may provide, in combination, a syringe having a barrel defining a bore for receiving a volume of liquid and a plunger that is movable through the bore; and a shield assembly having a cradle that is detachably operatively engageable about a portion of an exterior circumference of the barrel; and a shield operatively engaged with the cradle and configured to obscure a needle extending outwardly from one end of the barrel of the syringe. In one embodiment, a carriage engages the shield to the cradle. In one embodiment, the carriage is movably engaged with the cradle. In one embodiment, the shield is configured to be aesthetically pleasing to a young child. In one embodiment, the shield may be detachably engaged with the cradle.

BRIEF DESCRIPTION OF THE SEVERAL VIEWS OF THE DRAWINGS

Sample embodiments of the present disclosure are set forth in the following description, are shown in the drawings and are particularly and distinctly pointed out and set forth in the appended claims.

Similar numbers refer to similar parts throughout the drawings.

DETAILED DESCRIPTION

Referring to FIGS. 1 to 6, there is shown a first embodiment of a shield assembly for a syringe in accordance with the present disclosure, generally indicated at 10. Shield assembly 10 comprises a cradle 12, a carriage 14, and a shield 16. All of these components will be described in greater detail hereafter. Cradle 12 is configured to be operatively engaged around a portion of a circumference of a barrel of a syringe and the carriage 14 is configured to operatively engage the cradle 12. As will be described later herein, the carriage 14 is movably engaged with the cradle 12. Shield 16 is detachably engaged with one of the cradle 12 and the carriage 14 and is configured extend longitudinally downwardly from the cradle 12 and to cover the needle extending from the syringe at all times during use of the syringe. The shield 16 is configured to be aesthetically pleasing to a young child so as to reduce stress in the young child while they are either being injected with a substance or having their blood drawn using the syringe.

Figure 4:
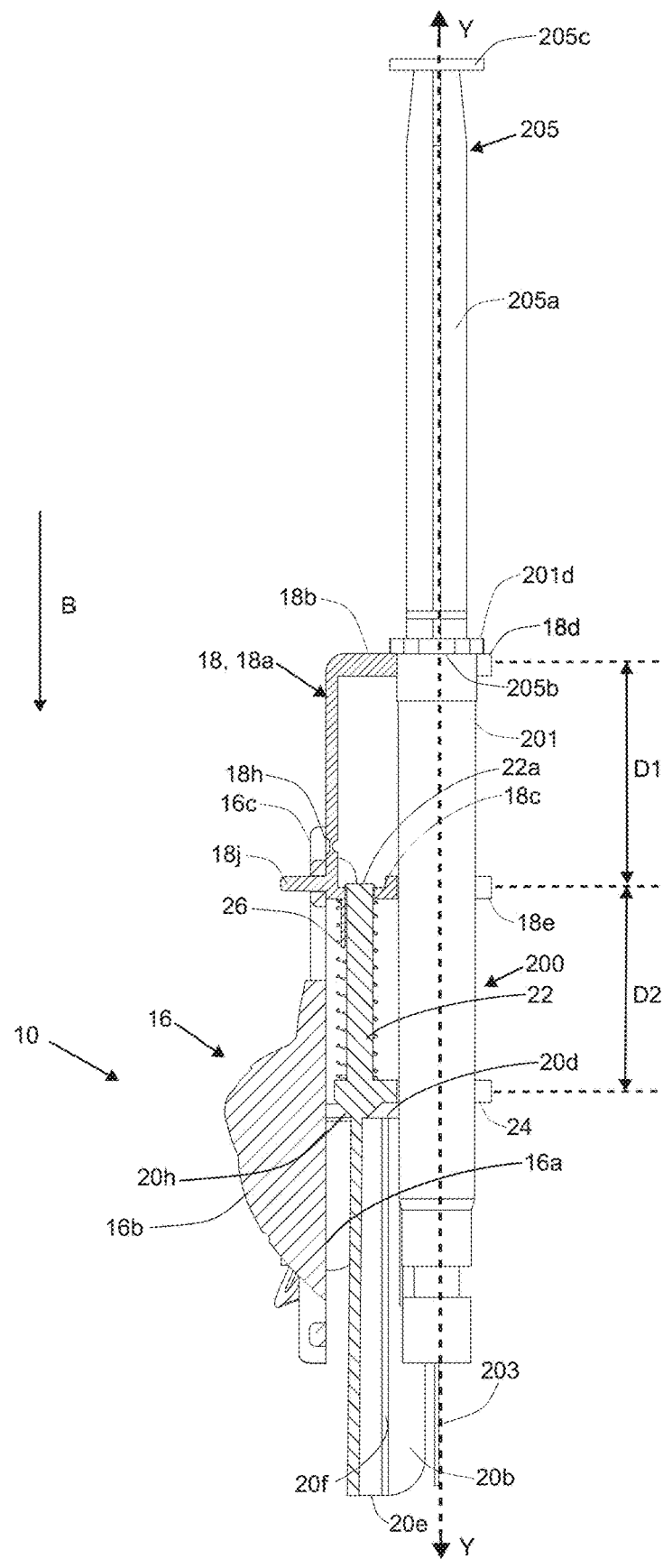
FIG. 4 is a longitudinal cross-section of the shield assembly shown engaged with the syringe and taken along line 4-4 of FIG. 3.
Figure 5:
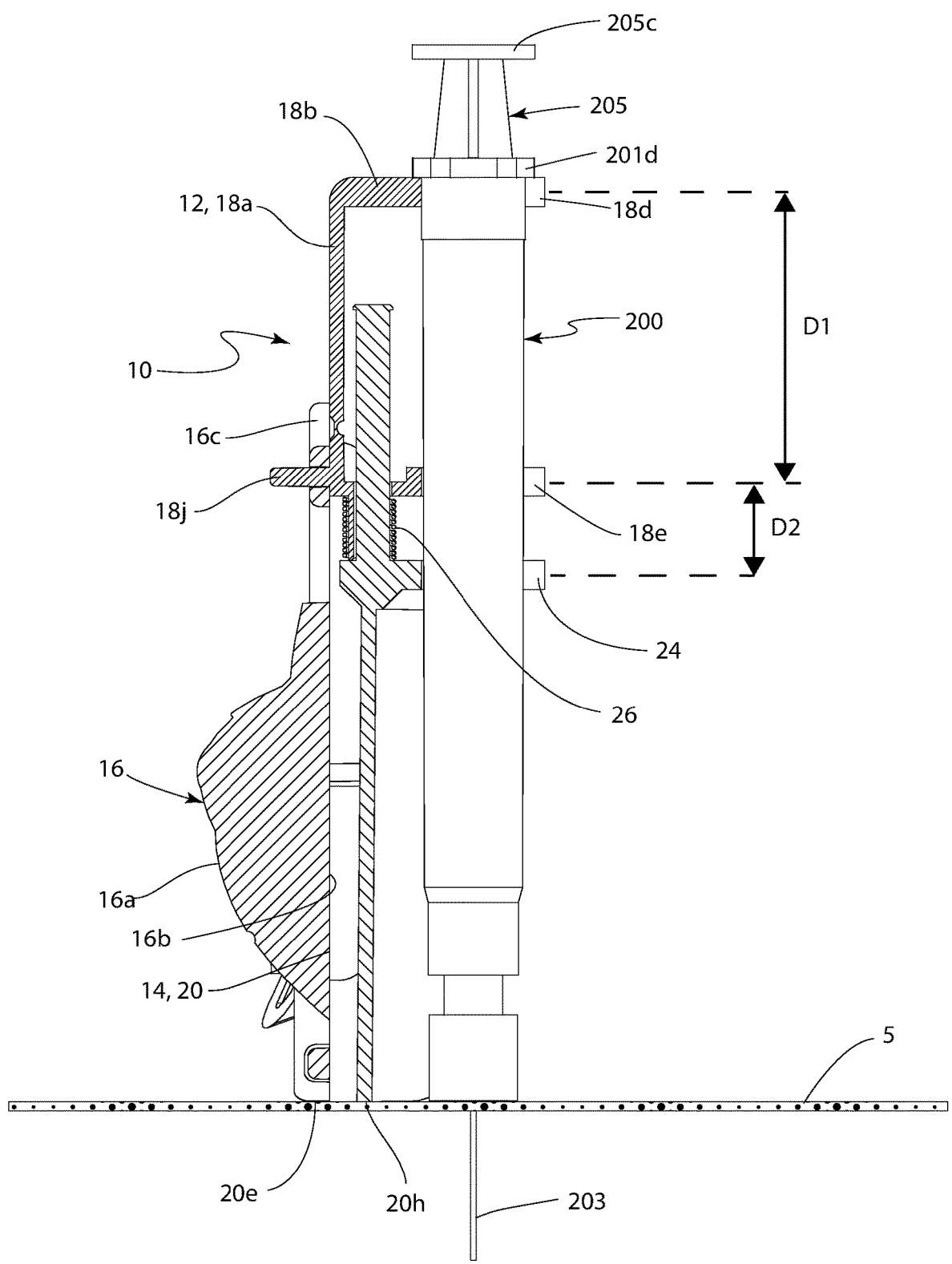
FIG. 5 is a longitudinal cross-section of the shield assembly and syringe similar to FIG. 4 but with the syringe in a second position during use with the plunger depressed and delivering a dose of medicine or vaccine into a patient's body.
Figure 6:
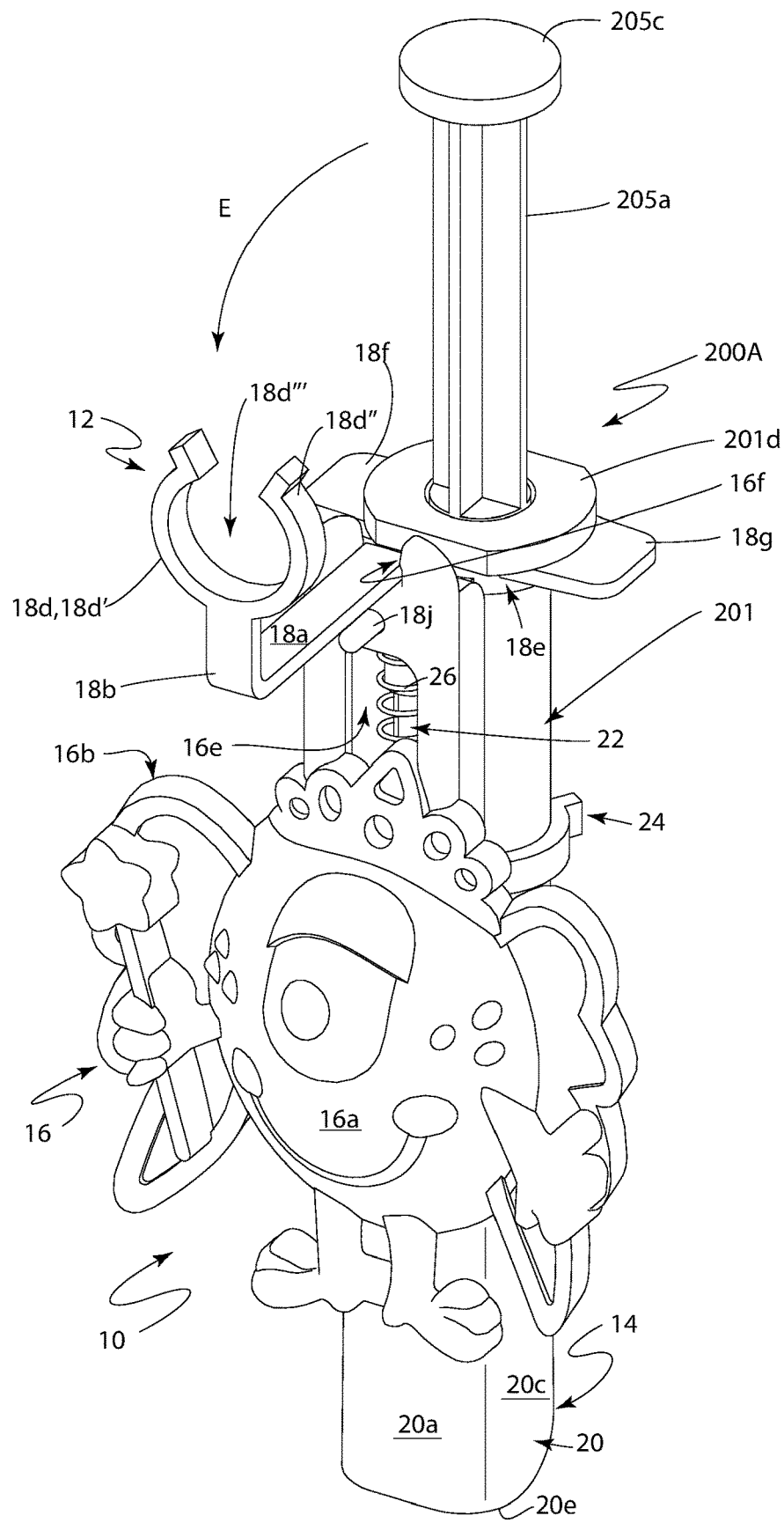
FIG. 6 is a front, top perspective view of the shield assembly of FIG. 1 shown engaged with a shorter length syringe than in FIG. 1A, and showing an upper part of the shield assembly pivoted to a second position.
Figure 6A:
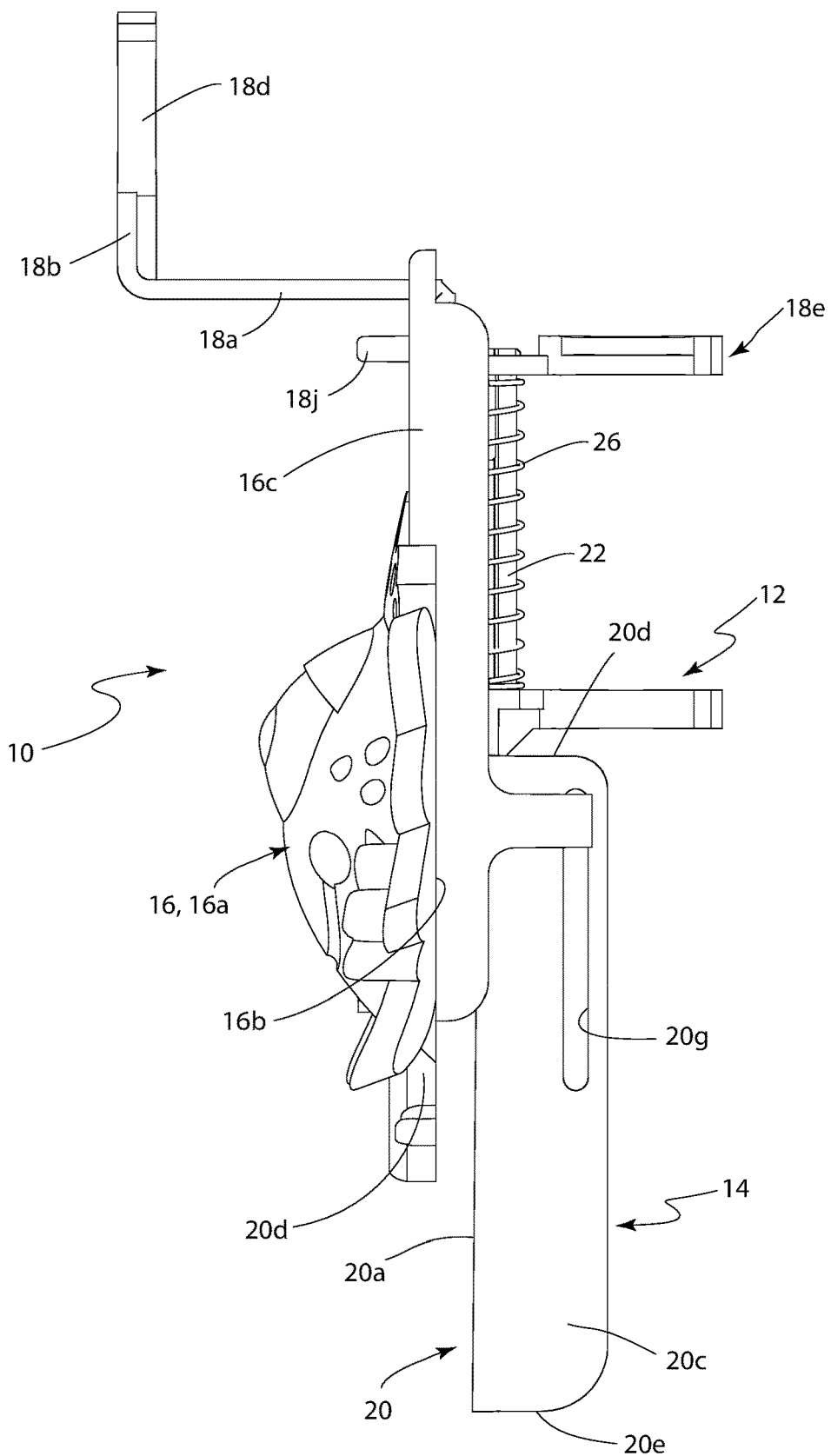
FIG. 6A is a left side elevation view of the shield assembly of FIG. 6 shown on its own.

As indicated above, shield assembly 10 is configured to be selectively engageable with a syringe. Syringe is any type of syringe known in the art. An exemplary syringe 200 is shown in FIGS. 1A, 3-5 and a further exemplary syringe 200A is shown in FIG. 6. The main difference between syringes 200 and 200A is the length thereof. This will be discussed later herein. It will be understood that shield assembly 10 may be engaged with a wide variety of other differently configured syringes and the specific illustrated configurations of syringes shown in the attached figures and described herein should in no way limit the scope of the presently described shield assembly 10.

Figure 1:
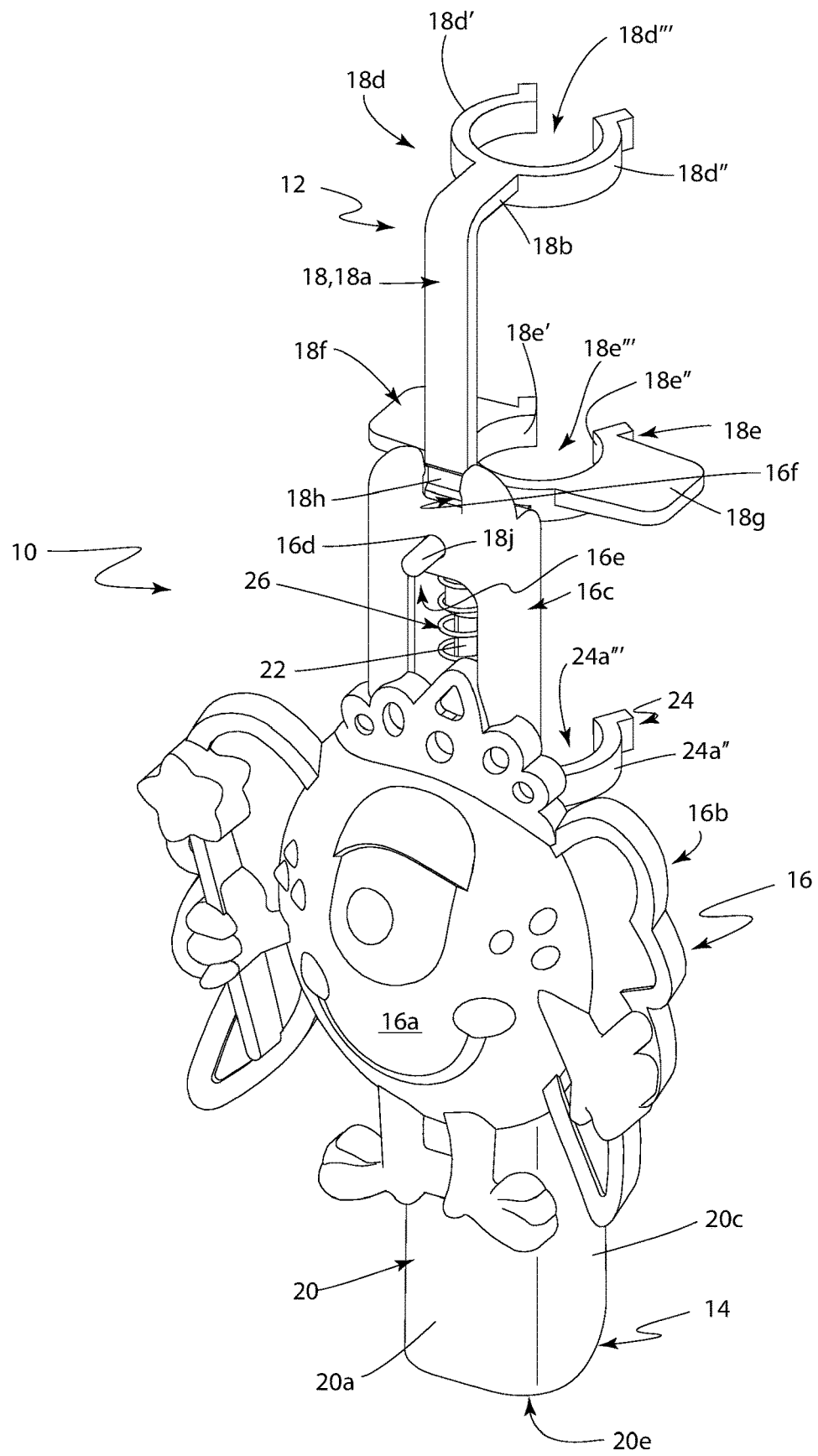
FIG. 1 is front, top perspective view of a first embodiment of a shield assembly for a syringe in accordance with the present disclosure, shown on its own.
Figure 1A:
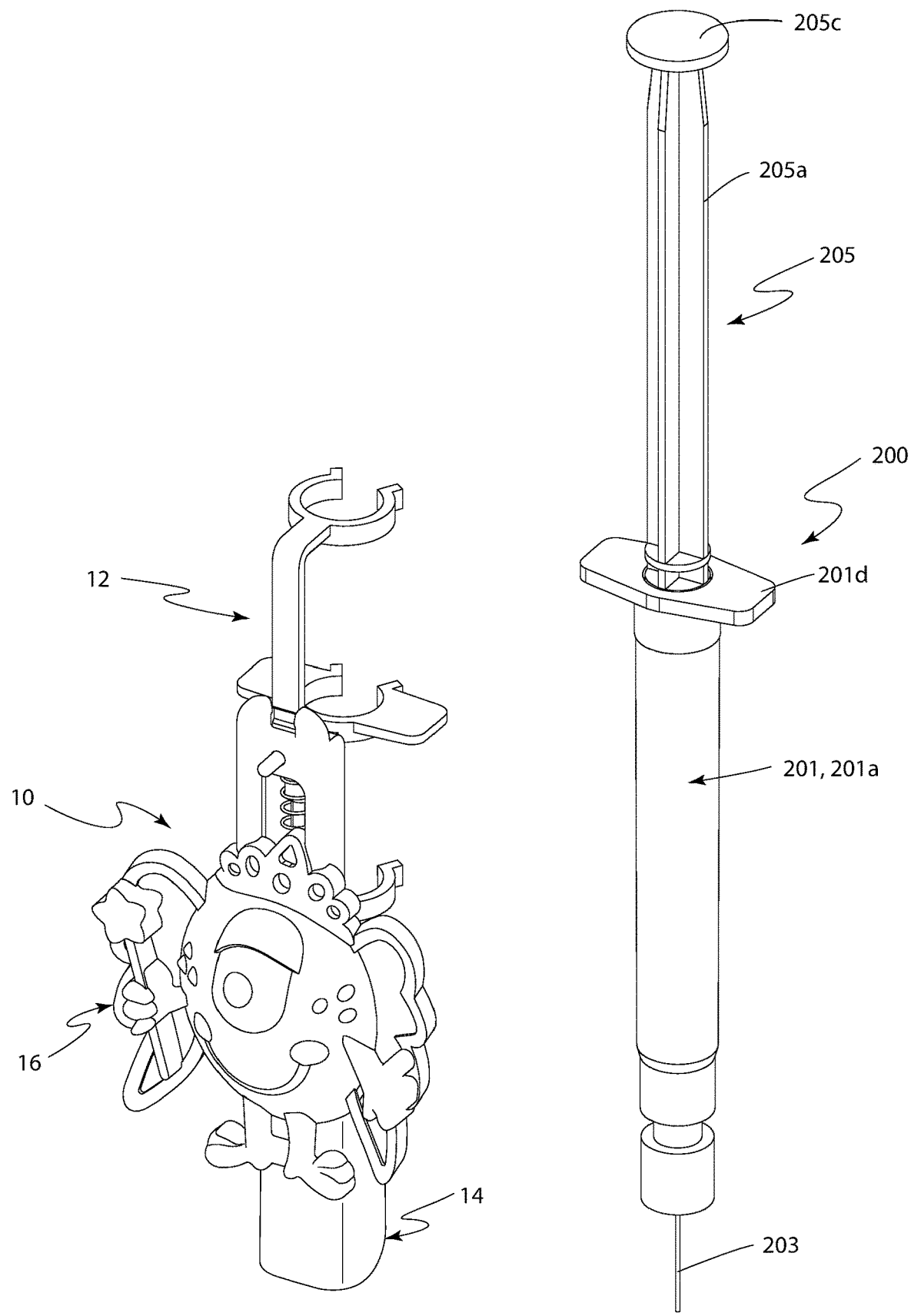
FIG. 1A is a front, top perspective view of the shield assembly of FIG. 1 shown alongside an exemplary syringe with which the shield assembly is able to be selectively engaged.
Figure 1B:
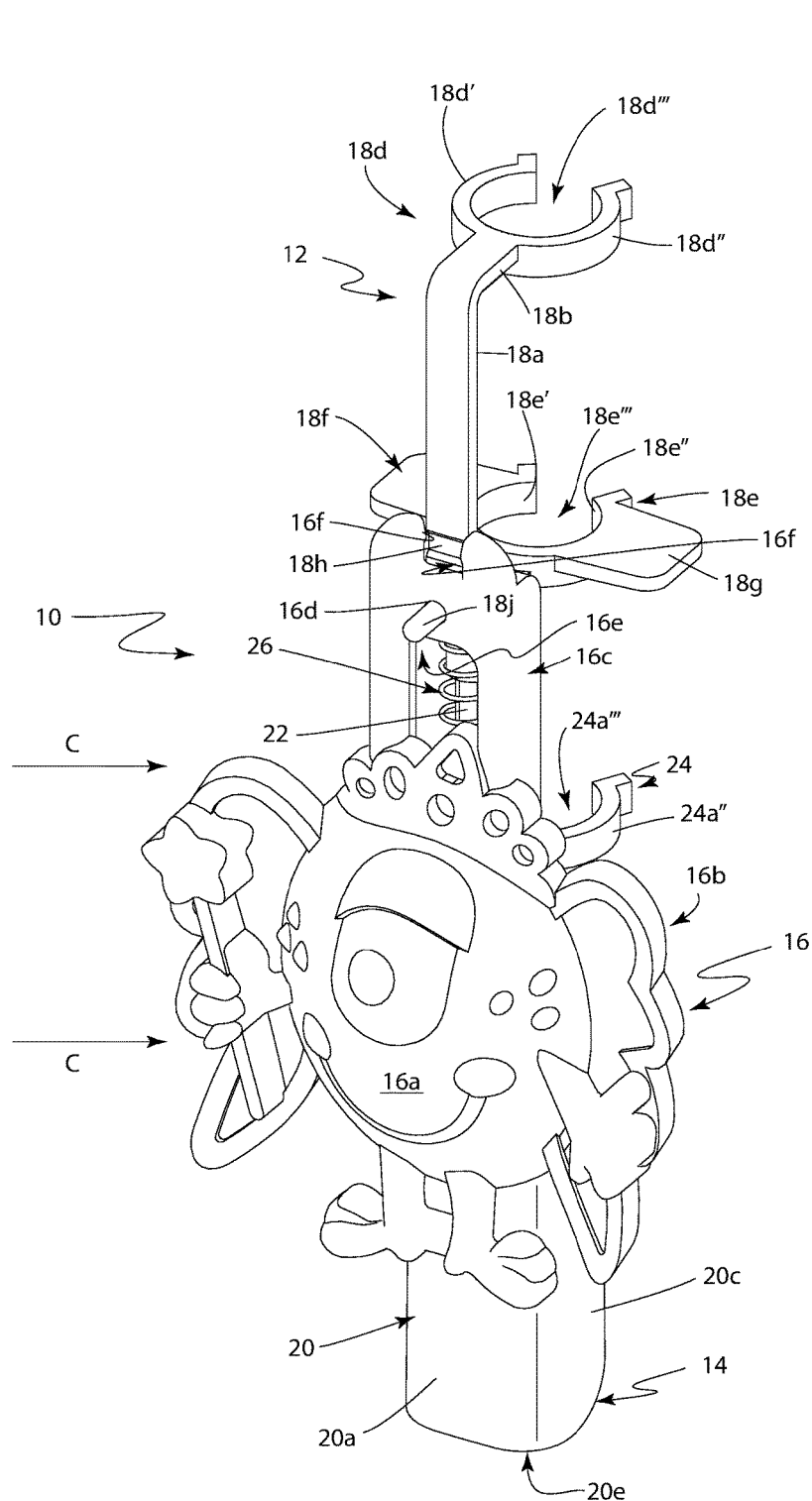
FIG. 1B is a front, top perspective view of the shield assembly of FIG. 1 shown alongside a partial longitudinal cross-section of the exemplary syringe with which the shield assembly is able to be selectively engaged.
Figure 1B:
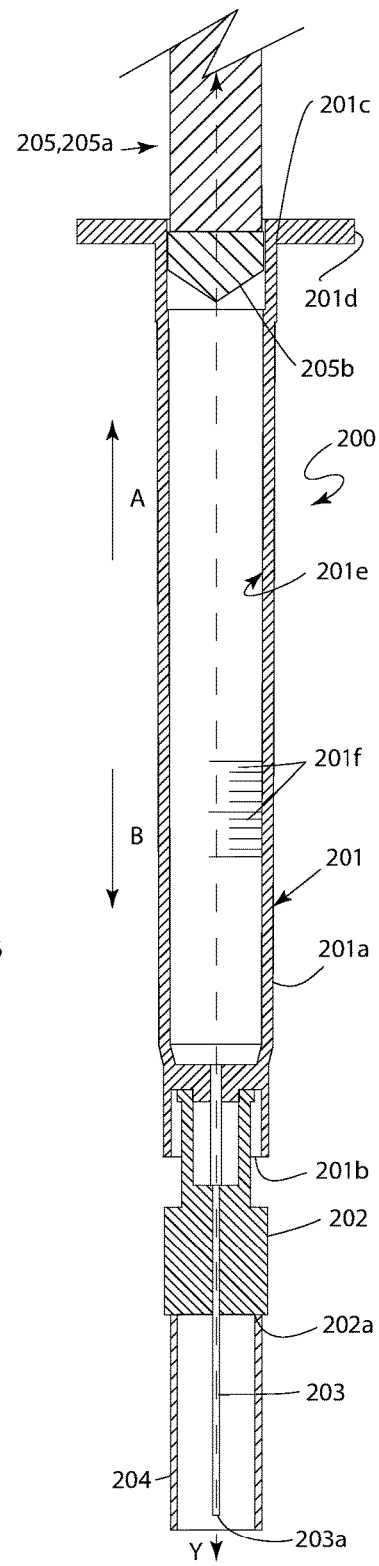
Figure 3:
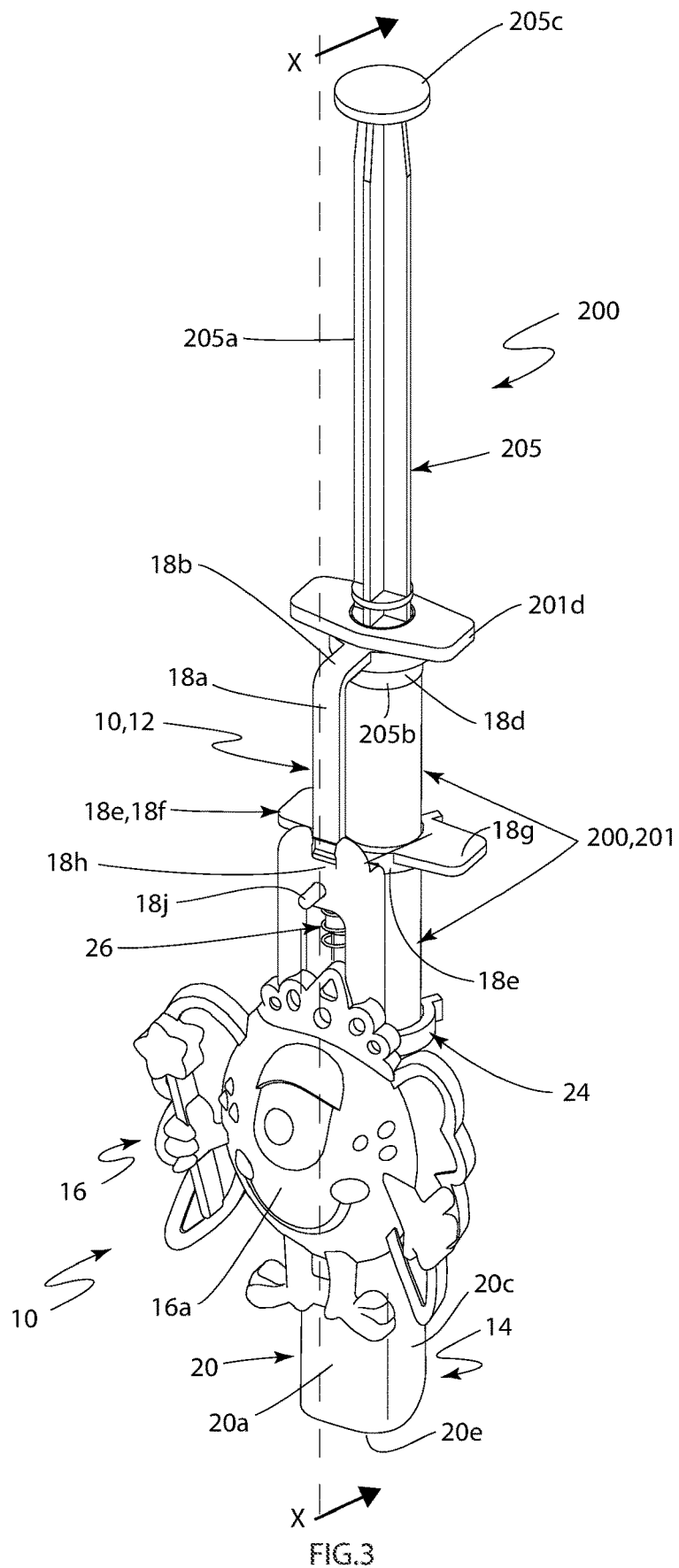
FIG. 3 is a front, top perspective view of the shield assembly shown engaged with the exemplary syringe and showing the syringe in a first position prior to use thereof.

Referring to FIGS. 1A and 3, syringe 200 includes a cylindrical barrel 201 having a circumferential wall 201a with a first end 201b and a second end 201c. A barrel flange 201d is provided proximate second end 201c and extends radially outwardly beyond the exterior wall 201a. Barrel 201 defines an interior bore 201e which extends from an opening (not numbered) in first end 201b to an aperture (not shown) defined in second end 201c. A plurality of volumetric markings 201f are provided on an exterior surface of wall 201a.

A tapered hub 202 is integrally formed with first end 201b of the barrel 201 and extends outwardly and forwardly therefrom along a longitudinal axis "Y" of syringe 200. Hub 202 terminates in a front end 202a located a distance longitudinally forwardly the first end 201b of barrel 201. Hub 202 defines a tapering bore (not numbered) therein which is in fluid communication with bore 201e of barrel 201 and terminates in an opening in front end 202a of hub. The hub's bore is therefore also in fluid communication with the aperture defined in second end 201c of barrel 201.

A hollow needle 203 is engaged with hub 202 in such a way that needle 203 extends outwardly from front end 202a of hub 202 and for a distance along longitudinal axis "Y" beyond hub 202. Needle 203 terminates in a tip 203a that defines an opening (not shown) therein. The opening in tip 203a is in fluid communication with bore 201e of barrel 201 via the bore of hub 202 and a bore (not shown) defined within needle 203. A protective cover (not shown) may be removably engaged over the tip 203a of needle 203 to keep the same clean and to prevent a medical professional from accidentally pricking themselves.

Referring still to FIGS. 1A and 3, syringe 200 also includes a plunger 205 that is movably engaged within bore 201e of barrel 201. Plunger 205 is inserted through the aperture (not shown) defined in second end 201c of barrel 201 and includes an elongate shaft 205a having a gasket 205b provided at a first end of shaft 205a and a plunger flange 205c extending radially outwardly from a second end of shaft 205a. Gasket 205b provided at the first end of shaft 205a seals off bore 201e to the outside environment and prevents any liquid within bore 201e from leaking out of the aperture in the second end 201c of barrel 201. Plunger 205 is movable in a first direction "A" (FIG. 1A) within bore 201e to draw air or liquid into bore 201e or is movable in a second direction "B" within bore 201e to push air or liquid out of bore 201e. This will be later described herein.

Referring to FIGS. 1, 2, 4, and 5, cradle 12 comprises a spine 18 that is generally U-shaped when viewed from the side. Spine 18 include a leg 18a, a first arm 18b, and a second arm 18c. Leg 18a extends along a plane that is parallel to longitudinal axis "Y" of syringe 200 (FIG. 5) when shield assembly 10 is engaged with syringe 200. First arm 18b and second arm 18c extend outwardly in a same direction from an inner surface of leg 18a and are oriented generally at right angles to the inner surface of leg 18a and thereby to longitudinal axis "Y". First arm 18a and second arm 18b are substantially parallel to one another and may be of generally a same length.

Shield assembly 10 is provided with components that enable the device to be snap-fittingly engaged around only a portion of the circumference of the syringe's barrel 201. Prior art devices were essentially tubular sleeves through which the syringe's needle and barrel had to be inserted and this could accidentally result in the needle being bent. The presently disclosed shield assembly 10 is quickly and easily snapped onto the barrel without coming into contact with needle 203 and therefore is less likely to compromise needle 203.

In order to snap-fittingly engage barrel 201, first arm 18b is provided with a first spring clip 18d and second arm 18c is provided with a second spring clip 18e. First spring clip 18d is generally U-shaped when viewed from above and includes a first finger 18d' and a second finger 18d" that bracket a first aperture 18d'". The free ends of first finger 18d' and second finger 18d" may be temporarily forced apart from one another and will then return back to their original orientation relative to one another when the force is removed.

Second spring clip 18e is differently configured from first spring clip 18d and includes a first finger 18e' and a second finger 18e" that bracket a second aperture 18e'". The free ends of first finger 18e' and second finger 18e" may be temporarily forced apart from one another and will then return back to their original orientation relative to one another when the force is removed. Second spring clip 18e differs from first spring clip 18d in that first finger 18e' includes a plate section 18f and second finger 18e" includes a plate section 18g. The plate sections 18f and 18g are integral with the respective first finger 18e' and second finger 18e" and extend laterally outwardly therefrom in a same plane as one another. The plate sections 18f, 18g together form a flange that allows a user to more readily grasp cradle 12 and manipulate the same. The plate sections 18f, 18g may also act as a stop for part of the syringe as will be discussed later herein.

Leg 18a has an outer surface and an inner surface and as mentioned earlier herein, the first arm 18d and second arm 18e extend outwardly from the inner surface of leg 18a. A first indentation (not numbered) is formed in the outer surface of leg 18a a short distance upwardly from second leg 18e. A second indentation (not numbered) is formed in the inner surface of leg 18a and is aligned with the first indentation. The provision of these two opposed indentations results in a portion of leg 18a being thinner than the remainder of the leg 18a. This thinner region 18h acts as a living hinge that when engaging the shield assembly 10 to syringe 200 allows the leg 18a to flex to a certain degree. The living hinge 18h also enables a first portion of the leg 18a and first spring clip 18d to be pivoted relative to a remaining second portion of the leg 18a. Living hinge 18h thereby enables the first portion of leg 18a to be moved to where it is oriented generally a right angles to longitudinal axis "Y" of shield assembly 10. The pivotal motion of leg 18a and purpose therefore will be described later herein.

Figure 2:
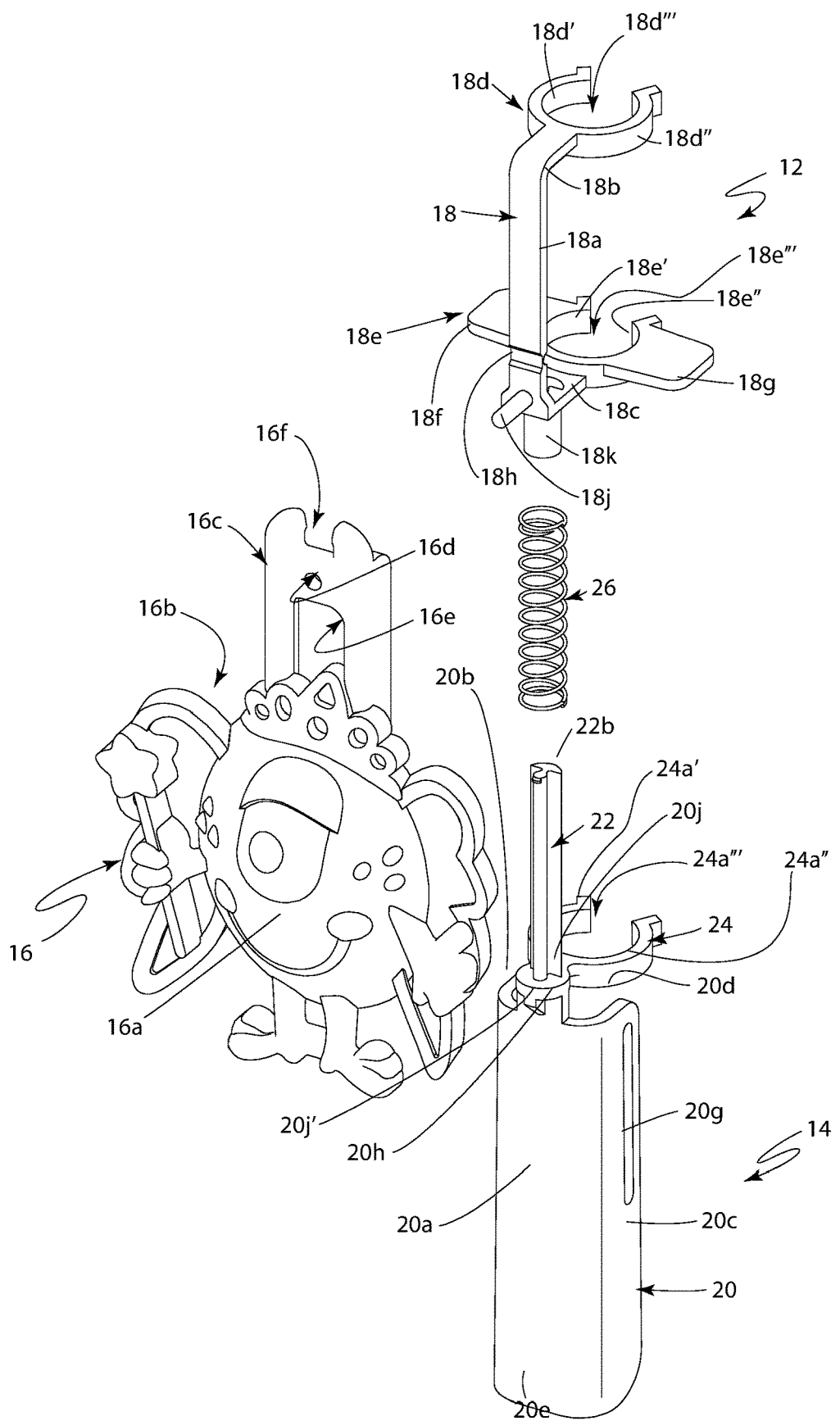
FIG. 2 is an exploded front, top perspective view of the shield assembly of FIG. 1.
Figure 2A:
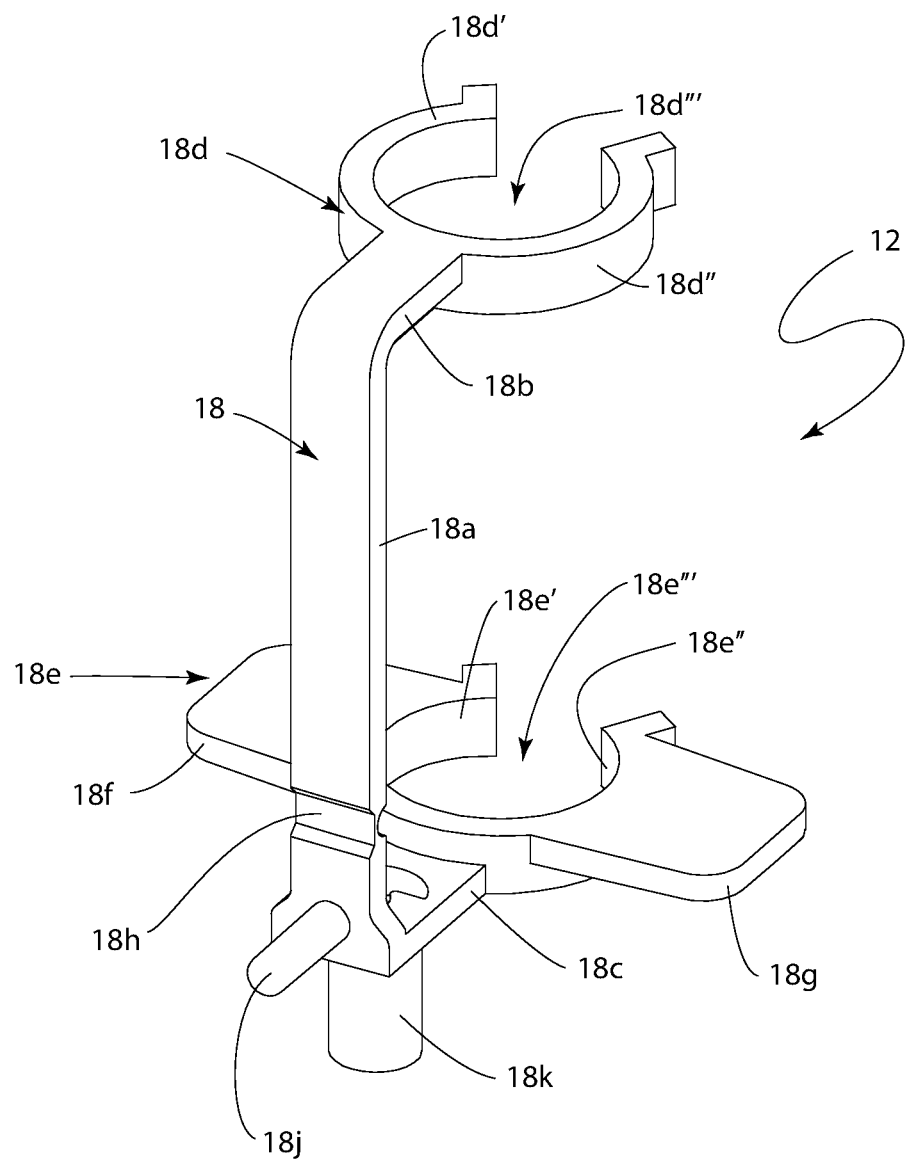
FIG. 2A is an enlarged front, top perspective view of the cradle of the shield assembly shown on its own.

FIG. 2 shows that a pin 18j extends outwardly from the outer surface of leg 18a in a location between living hinge 18h and second arm 18c. Pin 18j is oriented generally at right angles to the outer surface of leg 18a and thereby to longitudinal axis "Y". Pin 18j extends from leg 18a in an opposite direction relative to first arm 18b and second arm 18c. FIG. 1 shows that pin 18j is used to engage shield 16 to cradle 12. This will be discussed further later herein.

A post 18k (FIG. 2) extends downwardly from a bottom surface of second leg 18c. Post 18k is oriented generally parallel to leg 18a and thereby to longitudinal axis "Y". As best seen in FIGS. 4 and 5, post 18k includes an outer wall 18k' that bounds and defines slot 18k" therein. Slot 18k" may be generally T-shaped when post 18k is viewed from below. Slot 18k" extends from a free end of post 18k upwardly towards second arm 18c. Post 18k is shorter in length than leg 18a and is provided to enable cradle 12 and carriage 14 to be secured to one another. This will be described further herein.

Turning now to FIG. 2, carriage 14 includes a housing 20, a bar 22, and a spring clip 24. Housing 20 is an elongate U-shaped component having a rear wall 20a, first side wall 20b, and a second side wall 20c. Rear wall 20a will extend generally parallel to longitudinal axis "Y" of syringe 200 when shield assembly 10 is engaged with syringe 200. First side wall 20b and second side wall 20c extend outwardly from opposite side edges of rear wall 20a in generally a same direction as one another. Housing 20 also has a first end 20d and a second end 20e. Rear wall 20a, first side wall 20b, and second side wall 20c bound and define a channel 20f (FIG. 4) therebetween. Channel 20f extends parallel to longitudinal axis "Y". Each of the first side wall 20b and second side wall 20c may define a longitudinally oriented slot 20g (FIG. 2) therein that is in fluid communication with channel 20f.

A base member 20h (FIGS. 2 and 2B) extends upwardly from rear wall 20a and beyond first end 20d of housing 20. A platform 20j is provided at an outermost end of base member 20h. The platform 20j is enlarged relative to base member 20h and is oriented substantially at right angles to longitudinal axis "Y". One or more bracing members 20j' extends between a lower surface of platform 20j and the base member 20h. Platform 20j defines an aperture (not numbered) therein. Bar 22 is received through this aperture as will be described hereafter. The aperture defined in platform 20j is configured substantially identically to slot 18k" defined in post 18k of cradle 12.

Figure 2B:
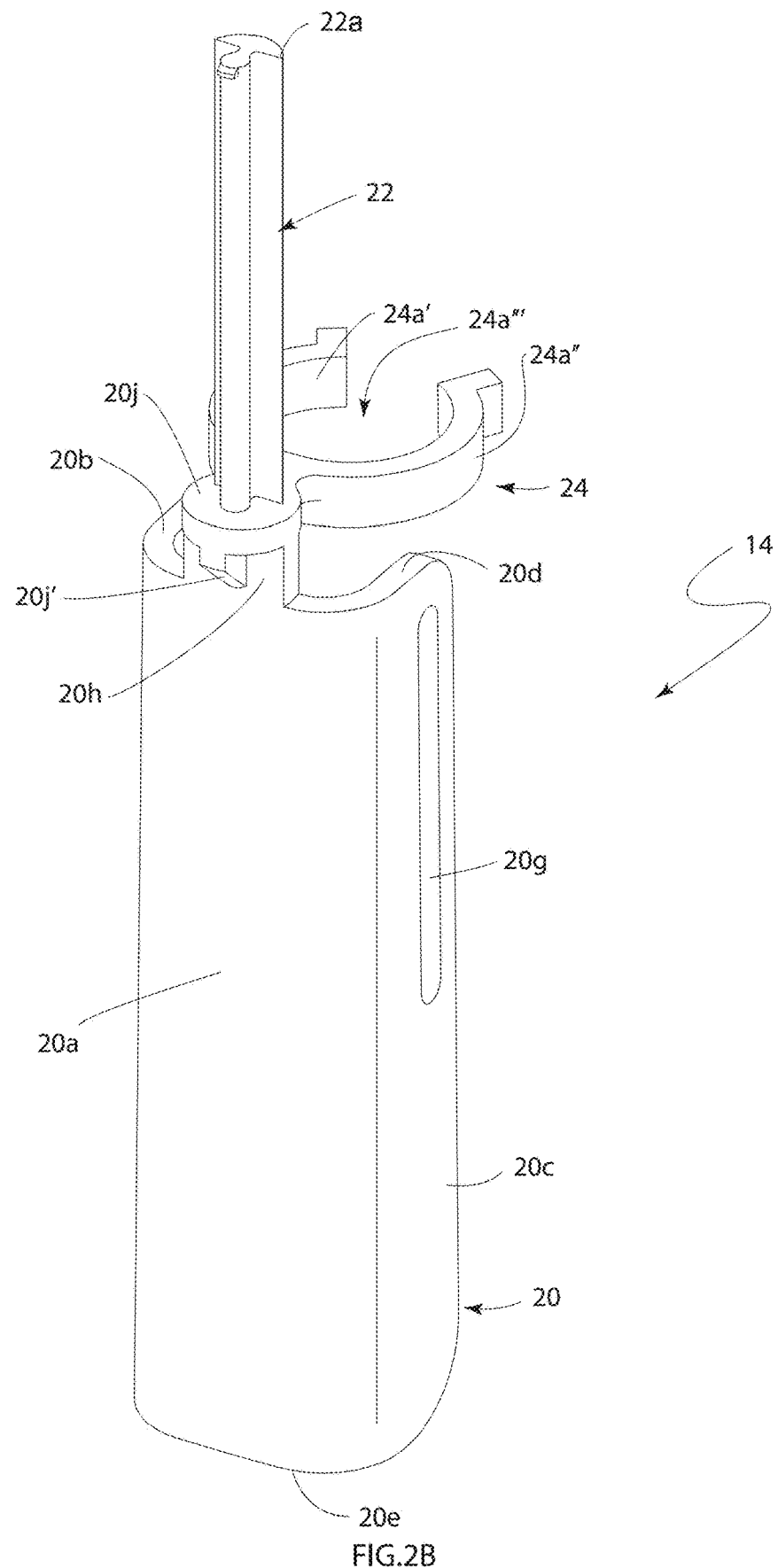
FIG. 2B is an enlarged front, top perspective view of the carriage of the shield assembly shown on its own.

Referring to FIGS. 2, 2B, and 4, bar 22 is an elongate member that extends outwardly from a first end 20d of housing 20 and has a free end 22b remote from first end 20d of housing 20 as is best seen in FIG. 4. Bar 22 is oriented in a plane generally parallel to longitudinal axis "Y" of syringe 200 when shield assembly 10 is engaged with syringe 200. Bar 22 is configured complementary in cross-section to the slot 18k" defined in the post 18k of cradle 12 and is received therethrough. Bar 22 is of a cross-sectional shape complementary to the cross-sectional shape of slot 18k". As best seen in the embodiment of the shield assembly 10 illustrated in FIGS. 2B and 4, bar 22 is T-shaped in cross-section and is configured to be interlockingly received through a complementary-shaped slot 18k" of post 18k.

It should be understood that slot 18k" and bar 22 may be other than T-shaped and will be fabricated to be complementary with one another in order to allow cradle 12 and carriage 14 to be interlockingly engaged together. For example, the bar 22 may be H-shaped or U-shaped and the slot 18k" will then be shaped and sized to interlock with one another. It will further be understood that in other embodiments, the bar may instead be provided on the cradle instead of carriage 14 and the bar will extend outwardly and downwardly from the cradle to be received through a complementary aperture defined in the carriage or in a post extending upwardly from the carriage.

When bar 22 is received through slot 18k" of cradle 12, the end 22b of bar 22 is oriented generally parallel to leg 18a and is located a distance inwardly from the inner surface of leg 18a. Bar 22 will therefore be located between the inner surface of leg 18a and the exterior surface of barrel 201 when shield assembly 10 is engaged with syringe 200. Because of the configuration of bar 22 and slot 18k", the end 22b of bar 22 is only able to be received through slot 18k" in one orientation. Furthermore, the end 22b preferably is configured to prevent bar 22 from being totally withdrawn from its engagement with post 18*k*. For example, the end 22*b* of bar 22 may include some type of locking member which prevents housing 20 from sliding out of slot 18*k*". The arrangement of cradle 12, carriage 14 and bar 22 is such that relative movement between cradle 12 and carriage 14 is enabled, as will be discussed hereafter.

As indicated earlier herein, spring clip 24 is provided on carriage 14. In particular, spring clip 24 is integral with and extends outwardly away from platform 20*j* of housing 20. This can best be seen in FIG. 4. Spring clip 24 is substantially similar in configuration to first spring clip 18*d* on cradle 12. Spring clip 24 is generally U-shaped when viewed from above and includes a first finger 24*a*' (FIG. 2) and a second finger 24*a*" that bracket an aperture 24*a*'". The free ends of first finger 24*a*' and second finger 24*a*" may be temporarily forced apart from one another and will then return back to their original orientation relative to one another when the force is removed. Spring clip 24 is generally aligned with housing 20 in such a way that the channel 20*f* of housing 20 at least partially aligns longitudinally with the aperture 24*a*'".

A coil spring 26 is engaged around the exterior surface of bar 22 and is positioned between platform 20*j* and a terminal end of post 18*k*. When cradle 12 and carriage 14 are engaged with one another via bar 22, spring clip 24 on carriage 14 is longitudinally aligned with first spring clip 18*d* (when in a first position such as in FIG. 1) and with second spring clip 18*e* on cradle 12. Spring clip 24 thereby effectively comprises a third spring clip on shield assembly 10.

FIG. 4 shows that first spring clip 18*d* is spaced a first distance "D1" from second spring clip 18*e*. The first distance "D1" is fixed and does not change. As mentioned earlier herein, carriage 14 is movable relative to cradle 12. In a resting position, such as shown in FIG. 1 or 4, when carriage 14 is furthest removed from cradle 12, spring clip 24 is spaced a second distance "D2" from second spring clip 18*e*. When force is applied to the second end 20*e* of housing 20 (as will be later described herein) there is relative movement between cradle 12 and carriage 14 and the second distance "D2" decreases. When there is relative movement between cradle 12 and carriage 14 in a first direction, spring 26 is compressed. When force is no longer applied to the second end 20*e* of housing 20, there will be relative movement between cradle 12 and carriage 14 in a second direction, and housing 20 will return to its resting position under the force of coil spring 26 returning to its uncompressed state.

Shield 16, as mentioned earlier herein is operatively engaged with cradle 12. Shield 16 may be formed in a variety of different shapes and sizes. In one embodiment, shield 16 is configured to include a substantially flat rear surface 16*a* (FIG. 4) and a 3-D front surface 16*b*. The front surface 16*b* may, for example, take the form of an aesthetically-pleasing, bright, and colorful 3-D character that will appeal to younger children. FIG. 1 for example, shows shield 16 configured in the shape of a smiling, one-eyed fairy. It will be understood that the configuration of shield 16 is exemplary only and a wide array of differently configured shields may be utilized as part of the shield assembly 10. Instead of a child-friendly 3-D character, shield 16 may be less child-pleasing and rather more appealing to older children, teenagers, or an adult. Alternatively, the decorative shield 16 may simply be a flat plate that has graphic indicia or text on it. For example, the decorative shield 16 may have the name of the medical facility provided on the front surface 16*b*. If the person being inoculated, injected, or having blood drawn is a younger child, then shield 16 may include a child-pleasing character or image and may not be 3-D in configuration.

Referring to FIG. 2, shield 16 includes a tab 16*c* that extends upwardly and outwardly beyond the represented character on the front surface 16*b*. Tab 16*c* is integral with the rear surface 16*a* and the front surface 16*b* and defines a hole 16*d*, slot 16*e*, and recess 16*f* therein. Each of the hole 16*d*, slot 16*e*, and recess 16*f* extends between the front surface 16*b* and rear surface 16*a* of shield 16. Hole 16*d* is shaped and sized to receive pin 18*j* of cradle 12 therethrough as illustrated in FIG. 1. Recess 16*f* is of a width suitable to receive leg 18*a* of cradle 12 therethrough when an upper leg 18*a* is pivoted about living hinge 18*h* from a first position (FIG. 1) to a second position (FIG. 6).

When it is desired to engage shield 16 with cradle 12, the user will simply align hole 16*d* in shield 16 with pin 18*j* on cradle 12 and will place rear surface 16*a* of shield 16 adjacent rear wall 20*a* of housing 20. The user will then push tab 16*c* of shield 16 towards the bar 22 of carriage 14 and rear wall 20*a* of housing 20 until rear surface 16*a* of shield 16 is adjacent bar 22 and rear wall 20*a*.

Referring to FIG. 1A, when a medical professional is about to use syringe 200 to inoculate or inject a person who is somewhat terrified of this procedure or is about to draw blood using syringe 200, the medical professional is able to selectively engage the shield assembly 10 with syringe 200. This is done so that the person receiving the injection or inoculation, or having blood drawn cannot actually see the needle 203 of syringe 200 (as will be described below). If the person being inoculated, injected, or having blood drawn, is older, then the decorative shield 16 may be omitted from the shield assembly 200 as the shield 16 is not the component of the shield assembly 10 that hides the needle 203. This job is actually performed by the housing 20. When a young child is being inoculated, for example, then a decorative shield 16 like the one illustrated in FIG. 1 is able to be engaged with shield assembly 10 to make the shield assembly 10 look less threatening to the young child.

When shield assembly 10 is ready to be engaged with syringe 200, cradle 12 and carriage 14 will already be interlockingly engaged with each other via bar 22. (This likely will occur in a factory that fabricates shield assembly 10.) Additionally, syringe 200 will be readied for the procedure. So, for example, if medicine or a vaccine is to be administered to a patient, then that medicine or vaccine will be drawn into the bore 201*e* of syringe 200 in a manner that is well known in the art. Needle 203 will have been covered with the protective cover 204 to keep the needle 203 clean and also to ensure that the medical professional doesn't accidentally prick themselves with needle 203.

Cradle 12 of shield assembly 10 is positioned adjacent barrel 201 of syringe 200 in such an orientation that housing 20 will overlay hub 202 and needle 203 as shown in FIG. 1A. The first spring clip 18*d* is positioned to be closer to barrel flange 201*d* than are the other spring clips 18*e* and 24. When shield assembly 10 and syringe 200 are in the correct orientation and shield assembly 10 is generally in the correct position relative to syringe 200, the free ends of the first spring clip 18*d*, second spring clip 18*e*, and third spring clip 24 are moved into contact with the exterior surface of the barrel's wall 201*a*. The user then pushes cradle 12 towards the barrel 201 in the direction indicated by arrows "C" in FIG. 1A. The application of this force tends to cause the first and second fingers of the first, second, and third spring clips 18*d*, 18*e*, 24 to temporarily move away from each other and receive the barrel 201 into the respective apertures bounded and defined by the first and second fingers of each spring clip. Cradle 12 may be moved along the barrel 201 in a first direction "A" towards the barrel flange 201d or away therefrom in the direction of arrow "B". This may be done to ensure the tip 203a of needle 203 is located a distance inwardly from second end 20e of housing 20, that needle 203 is located within channel 20f of housing 20, and housing 20 is shrouding needle 203. The rear wall 20a and side walls 20b, 20c of housing 20 effectively ensure that a patient cannot see the needle 203.

If a shield 16 is to be engaged on shield assembly 10, this may be done prior to engaging cradle 12 on syringe 200 or after engaging cradle 12 on syringe 200. The medical professional will simply select the shield 16 they wish to use (possibly from a box of differently configured shields) and will align the hole 16d in tab 16c with pin 18j of cradle 12. Shield 16 will then be pushed downwardly toward housing 20 as previously described herein, in order to ensure that the flat rear surface 16a of shield 16A is adjacent rear wall 20a of housing 20.

At this point, the shielded syringe 200 (as shown in FIGS. 3 and 4) is ready for use. Referring to FIGS. 3, 4, and 5, the medical professional will rest the second end 20e of housing 20 against the skin "S" of the patient proximate the site where the needle 203 is to pierce the skin "S". Slight pressure is then applied to the shielded syringe 200 in a direction moving towards the skin "S", as indicated by arrow "D" in FIG. 4. Cradle 12 grips syringe 200 and will therefore move in unison with syringe 200. Because the second end 20e of the housing 20 is prevented from moving, when the syringe 200 is moved in the direction "D", cradle 12 will tend to move towards carriage 14 because bar 22 slides further through the aperture defined in platform 20j and further into channel 20f of housing 20. As cradle 12 moves in the direction "D", spring 26 is compressed. Continued movement of syringe 200 in the direction "D" will cause the tip 203a of needle 203 to pierce the skin "S".

Even if the patient is looking directly at the shielded syringe 200 during the above-described steps, the housing 20 shrouds the needle 203 and the patient is therefore unlikely to even catch a glimpse of the needle 203 as it pierces their skin. If the shield 16A is engaged with the shield assembly 200, all the patient will see is the little character on the shield 16 moving towards their skin "S". This obscuring of the needle 203 helps to alleviate some of the anticipatory fear that the patient might otherwise experience.

Once the needle tip 203a has pierced the skin and been inserted to the required depth for administration of the particular medicine or vaccine, for example, the medical professional will depress the plunger 205 into the barrel 201 (moving the same in the direction "D", and will thereby deliver the dose of medicine or vaccine from the barrel's bore 201e and into the patient's body through needle 203. Alternatively, if blood, for example, is to be drawn, when the needle 203 is in the appropriate location in the patient's tissue, the plunger 205 will be pulled in an opposite direction to arrow "D" and blood will be drawn through needle 203 and into bore 201e of barrel 201.

When the injection, inoculation, or drawing of blood is over, pressure on the syringe 200 toward the skin will be released as the syringe 200 is oved in the opposite direction to arrow "D", thus withdrawing the needle 203 from the patient's body. As the syringe 200 is withdrawn, the force in the direction "D" is removed from cradle 12 and/or carriage 14 and the compressed spring 26 will return to its original shape and position. This will, in turn, cause carriage 14 to move away from cradle 12 and back to its original at-rest position. It should be noted that as carriage 14 moves away from cradle 12 it continues to shroud needle 203 and thereby tends to prevent the patient from even catching a glimpse of the needle 203. The cover 204 may then be placed over the tip 203a once again to prevent accidental injury by pricking.

If the patient is a young child, the medical professional may then disengage the shield 16 from cradle 12 and give the same to the young child as a reward for cooperating with the medical procedure or to help emotionally soothe the patient.

The shield assembly 10 may be disengaged from the syringe 200 by simply pulling the cradle 12 in a direction moving at right angles away from barrel 201 in an opposite direction to arrows "C" (FIG. 1A) such that the first and second fingers of each of the first spring clip 18d, second spring clip 18e, and third spring clip 24 spread apart and allow the barrel 201 to be withdrawn therefrom. Shield assembly 10 may be sterilized and then attached to a second syringe or shield assembly 10 may be appropriately discarded or recycled.

FIG. 6 shows the shield assembly 10 engaged with a syringe 200A that is substantially shorter than the syringe 200 shown in FIG. 3. Syringe 200A is substantially identical to syringe 200 except that it is shorter in length than syringe 200. Consequently, all components on syringe 200A are essentially similar to the components of syringe 200 and will therefore be identified by the same reference characters in the figures and this description.

Referring still to FIG. 6, in order to prevent first spring clip 18d from interfering with the movement of plunger 205 of the shorter syringe 200A, the medical professional will grasp leg 18a and will pivot the same about living hinge 18h in a direction moving away from syringe 200A. This pivotal motion is indicated by arrow "E" in FIG. 6. Leg 18a is pushed downwardly into recess 16f defined in tab 16c of shield 16 and frictionally retained therein and therefore out of the medical professional's way. Syringe 200A may then be used in substantially the same manner as syringe 200 described above. If a shield 16 is not utilized, then the medical professional will simply push the leg 18a downwardly to a sufficient degree (even past 90° relative to the leg's initial orientation) in order to move the leg 18a and first spring clip 18d out of the plunger's way.

Referring now to FIGS. 7 through 11, a second embodiment of a shield assembly in accordance with the present disclosure is illustrated, generally indicated at 110. Shield assembly 110 comprises a cradle 112, a carriage 114, and a shield 16. Shield 16 is substantially identical to shield 16 illustrated in FIGS. 1-6 and described above and therefore will not be described in any further detail.

Figure 8:
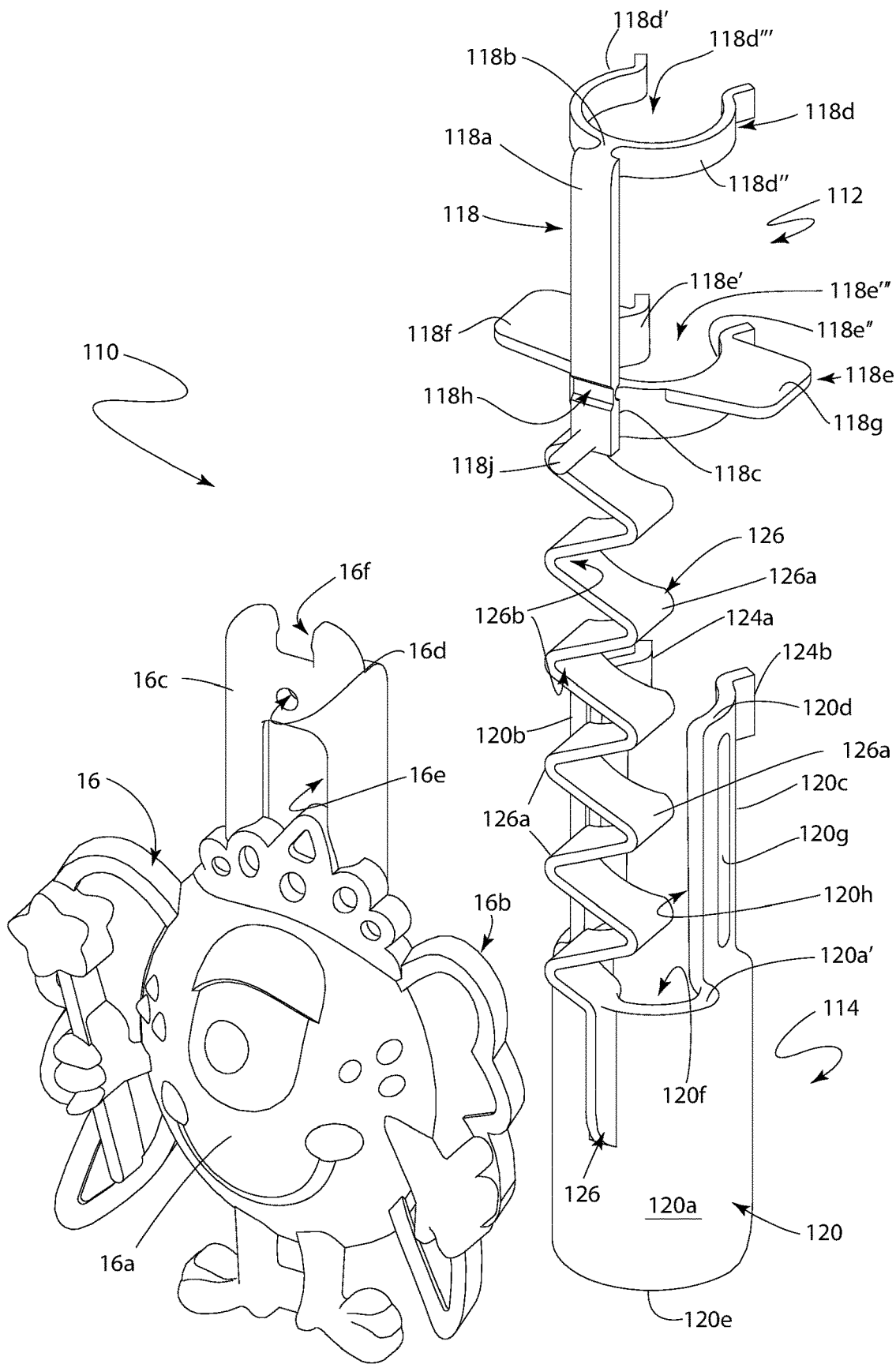
FIG. 8 is an exploded front, top perspective view of the shield assembly of FIG. 7.
Figure 9:
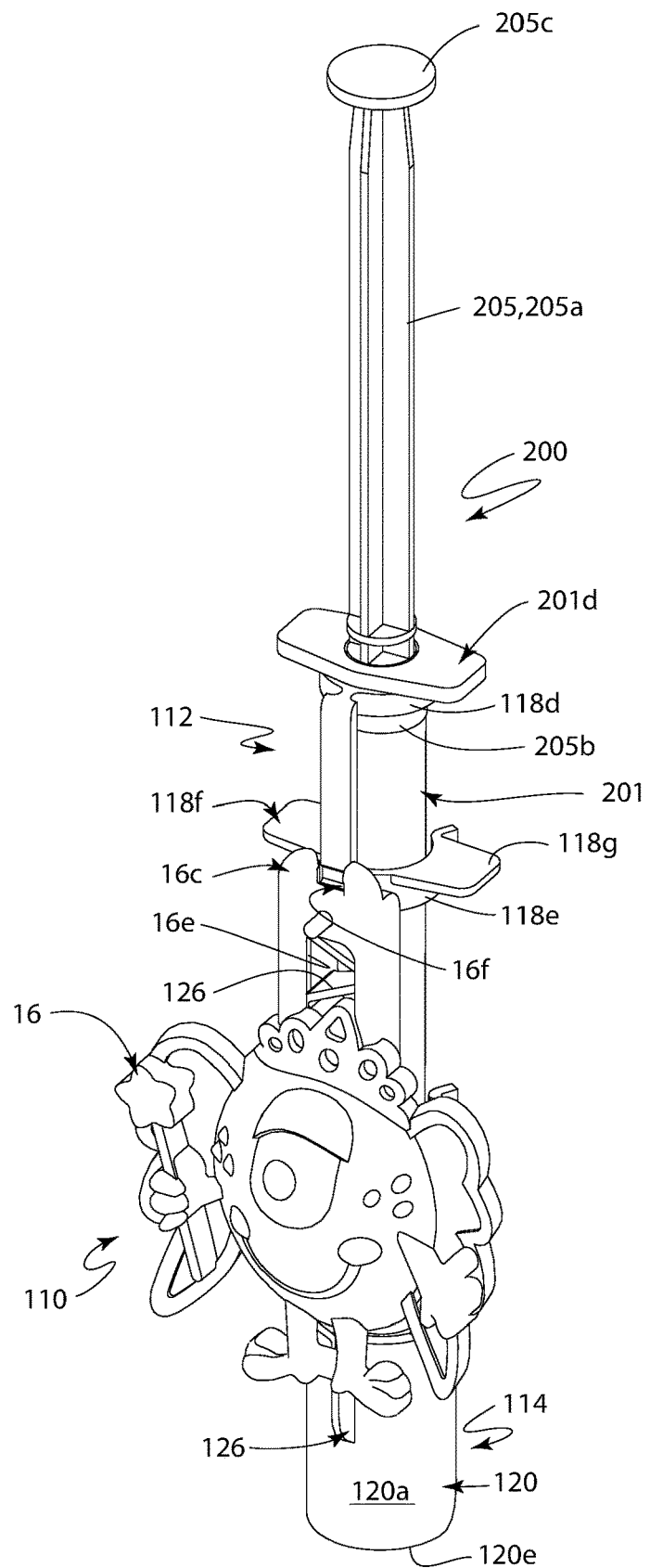
FIG. 9 is a front, top perspective view of the shield assembly of FIG. 7 shown engaged with a syringe similar to that shown in FIG. 1A.

Referring particularly to FIG. 8, cradle 112 is substantially identical in every way to cradle 12 except as will be described hereafter. As such, cradle 112 comprises a spine 118 that is generally U-shaped when viewed from the side. Spine 118 include a leg 118a, a first arm 118b, and a second arm 118c. Leg 118a extends along a plane that is generally parallel to longitudinal axis "Y" (FIG. 10) of syringe 200A and first arm 118b and second arm 118c extend outwardly in a same direction from an inner surface of leg 118a and are oriented generally at right angles to the inner surface and to longitudinal axis "Y". First arm 118a and second arm 118b are substantially parallel to one another and may be of generally a same length.

First arm 118b terminates in a first spring clip 118d and second arm 118c terminates in a second spring clip 118e. First spring clip 118d is generally U-shaped when viewed from above and includes a first finger 118*d'* and a second finger 118*d"* that bracket a first aperture 118*d'''*. The free ends of first finger 118*d'* and second finger 118*d"* may be temporarily forced apart from one another and will then return back to their original orientation relative to one another when the force is removed.

Second spring clip 118*e* is differently configured from first spring clip 118*d* and includes a first finger 118*e'* and a second finger 118*e"* that bracket a second aperture 118*e'''*. The free ends of first finger 118*e'* and second finger 118*e"* may be temporarily forced apart from one another and will then return back to their original orientation relative to one another when the force is removed. Second spring clip 118*e* differs from first spring clip 118*d* in that first finger 118*e'* includes a plate section 118*f* and second finger 118*e"* includes a plate section 118*g*. The plate sections 118*f* and 118*g* are integral with the respective first finger 118*e'* and second finger 118*e"* and extend laterally outwardly therefrom in a same plane as one another. The plate sections 118*f*, 118*g* together form a flange that allows a user to more readily grasp cradle 112 and manipulate the same. The plate sections 118*f*, 118*g* may also act as a stop for part of the syringe as will be discussed later herein.

Figure 10:
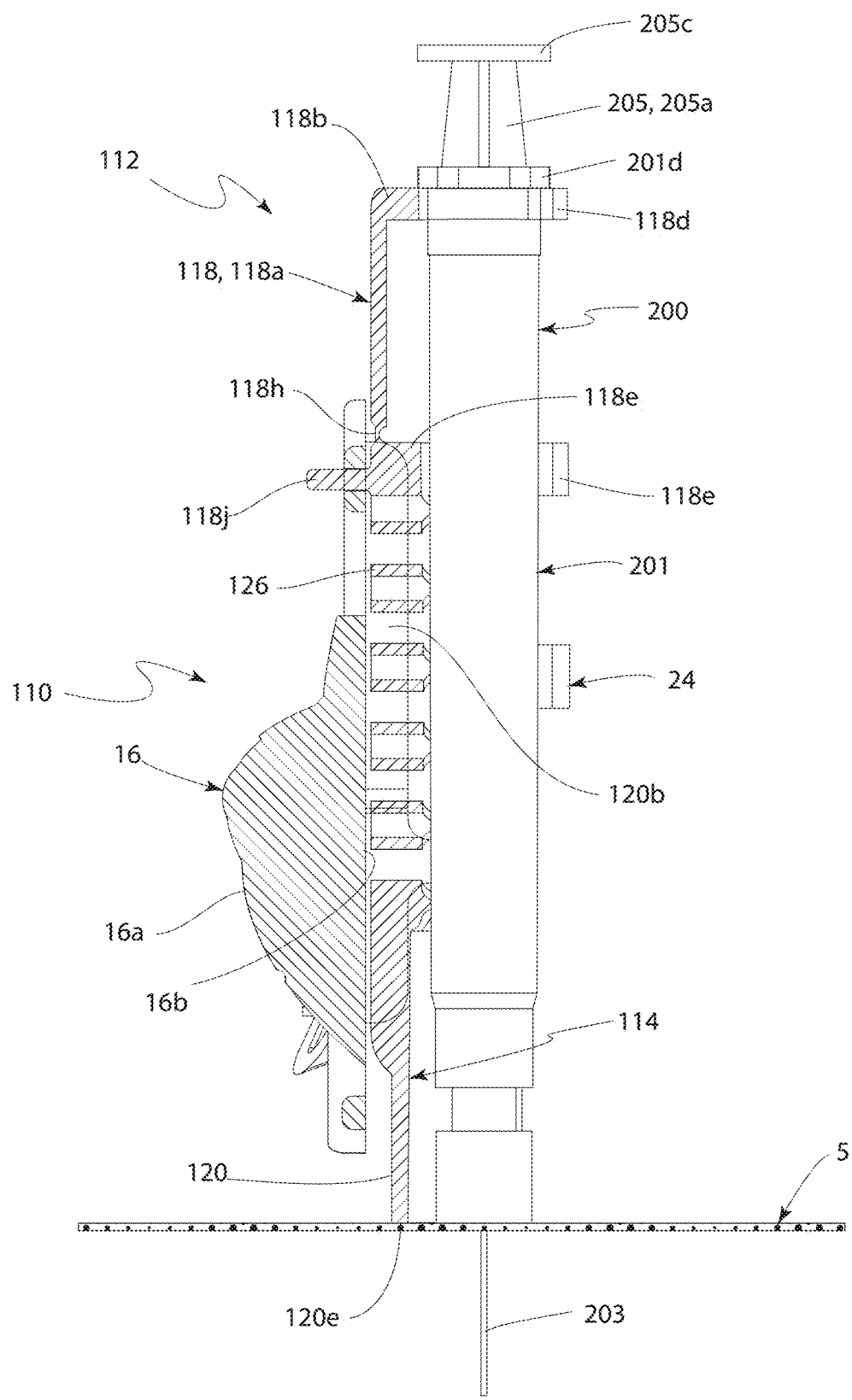
FIG. 10 is a longitudinal cross-section of the shield assembly and syringe FIG. 7 engaged with the syringe as in FIG. 9 but with the syringe shown in use and located in a second position.
Figure 11:
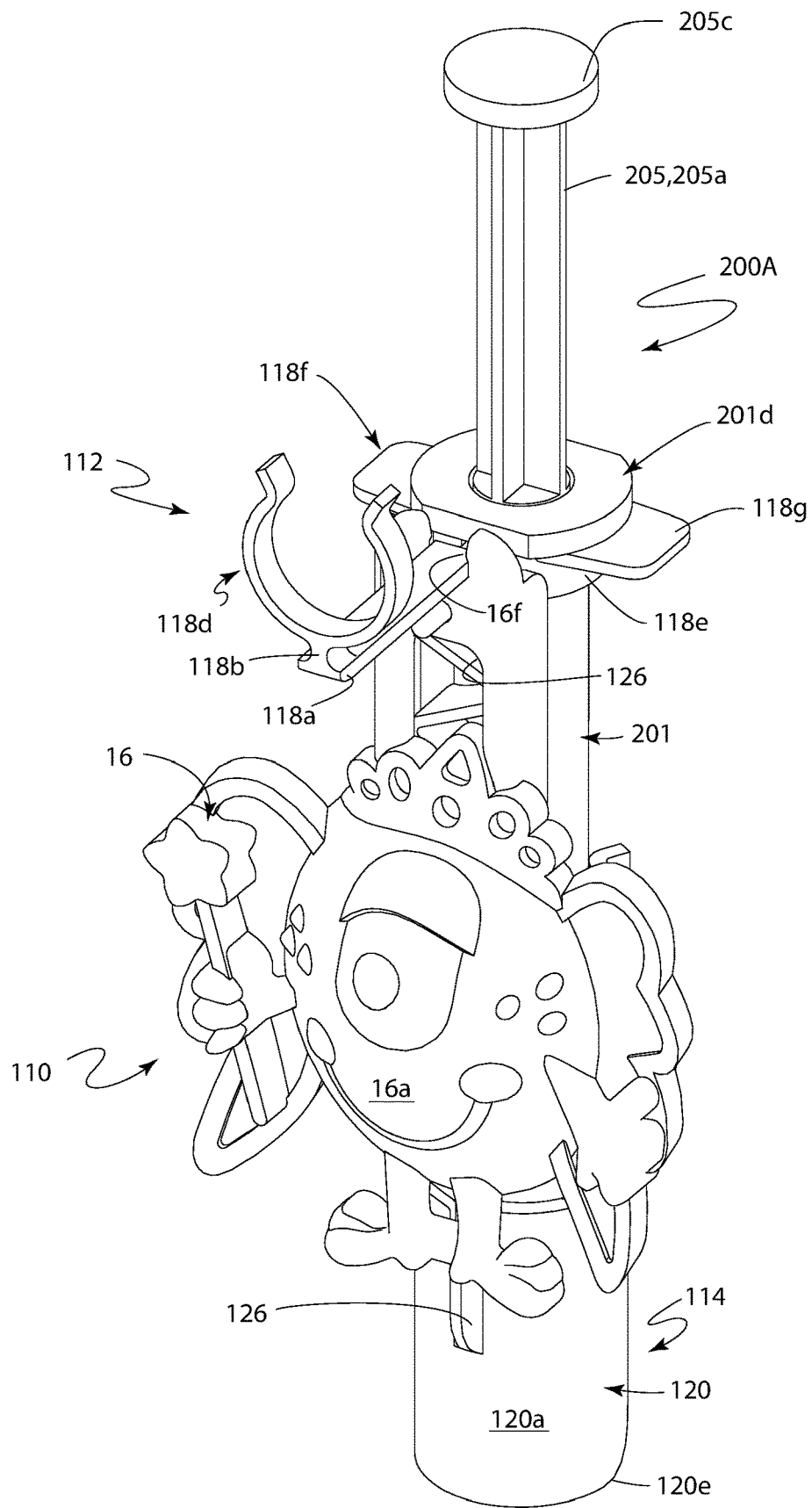
FIG. 11 is a front, top perspective view of the shield assembly of FIG. 7 shown engaged with a shorter syringe and showing the upper part thereof pivoted to a second position.

Leg 118*a* has an outer surface and an inner surface and as mentioned earlier herein, the first arm 118*d* and second arm 118*e* extend outwardly from the inner surface of leg 118*a*. A first indentation (not numbered) is formed in the outer surface of leg 118*a* a short distance upwardly from second leg 118*e*. A second indentation (not numbered) is formed in the inner surface of leg 118*a* and is aligned with the first indentation. The provision of these two opposed indentations results in a portion of leg 118*a* being thinner than the remainder of the leg 118*a*. This thinner region 118*h* acts as a living hinge that when engaging the shield assembly 10 to syringe 200 allows the leg 118*a* to flex to a certain degree. The living hinge 118*h* also enables a first portion of the leg 118*a* and first spring clip 118*d* to be pivoted relative to a remaining second portion of leg 118*a*. FIG. 10 shows the leg 118*a* aligned along a plane parallel to longitudinal axis "Y" while FIG. 11 shows the leg 118*a* pivoted through about 90° relative to the longitudinal axis "Y". The pivotal motion of leg 118*a* is similar to the pivotal motion and purpose of leg 18*a* and therefore will not be further described herein in particular detail.

Figure 7:
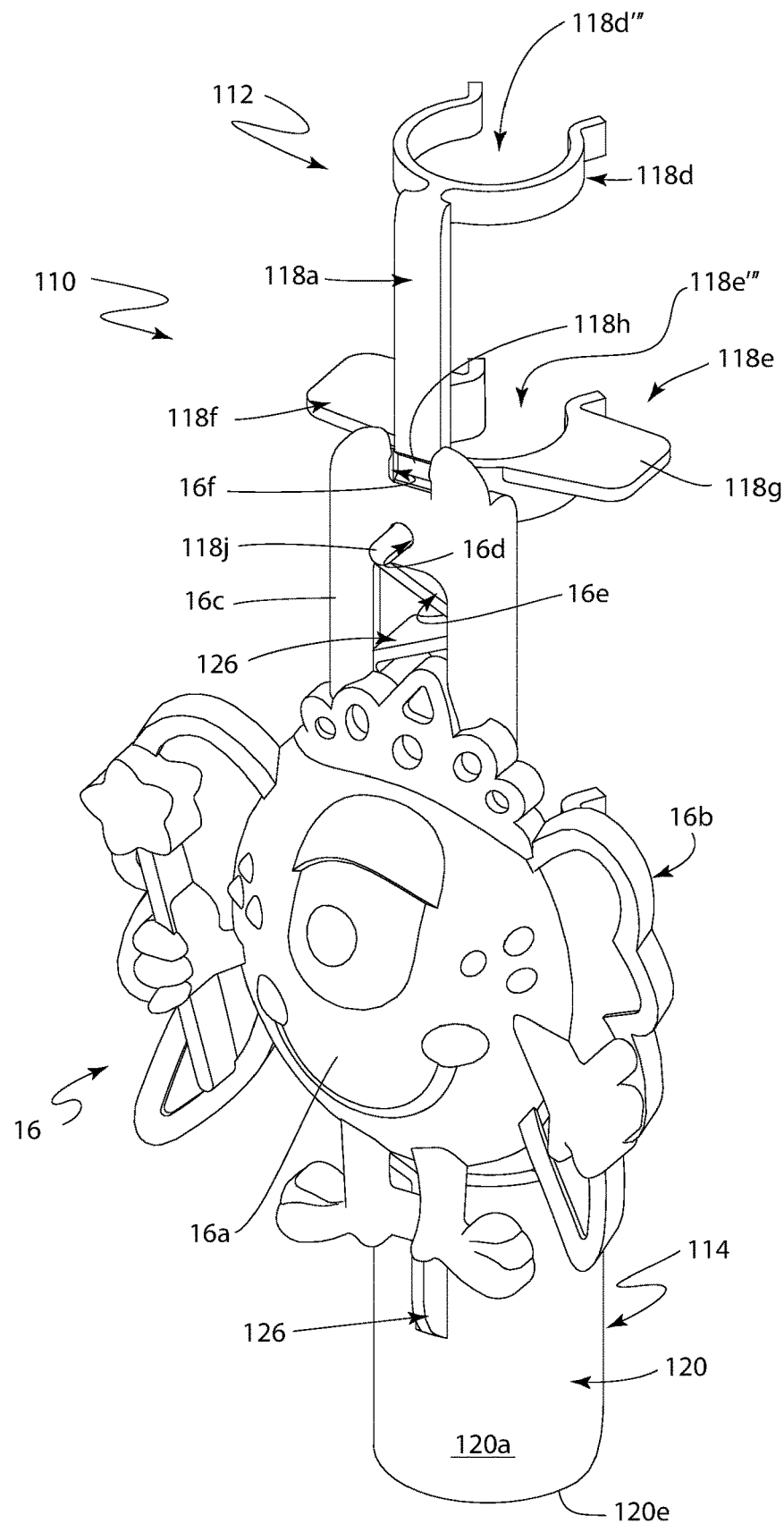
FIG. 7 is a front, top perspective view of a second embodiment of a shield assembly for a syringe in accordance with the present disclosure, shown on its own.

FIG. 8 shows that a pin 118*j* extends outwardly from the outer surface of leg 118*a* in a location between living hinge 118*h* and second arm 118*c*. Pin 118*j* is oriented generally at right angles to outer surface of leg 118*a* and thereby to longitudinal axis "Y". The first portion of leg 118*a* extends from leg 118*a* in an opposite direction relative to first arm 118*b* and second arm 118*c*. FIG. 7 shows that pin 118*j* is used to engage shield 16 to cradle 112. This engagement is similar to the manner in which shield 16 is engaged with cradle 12 and therefore will not be described in detail herein.

Cradle 112 differs from cradle 12 in that there is no post 12*k* extending downwardly from the second arm 118*c* thereof. Instead, a first end of a spring member 126 is integrally formed with cradle 112 and extends downwardly from second arm 118*c* and a second end of the spring member 126 is integrally formed with carriage 114. Spring member 126 therefore permanently connects cradle 112 to carriage 114 and is not separable from either component.

Spring member 126 comprises a band of material that generally is in the configuration of a sine wave and is formed into a series of undulating peaks 126*a* and valleys 126*b*. The band of material is selectively compressible when force is applied thereto but is also sufficiently resilient enough to return to its original shape and position when the force is removed.

Referring still to FIG. 8, carriage 114 is differently configured to carriage 14 in a number of ways. Carriage 114 includes a housing 120 having an exterior wall 120*a* that is generally U-shaped when viewed from below. The wall incudes a first wing 120*b* and a second wing 120*c* that extend upwardly from exterior wall 120*a* and are integrally formed therewith. The wings 120*b*, 120*c* terminate in a first end 120*c*. Wall 120*c* also has a second end 120*e* located a distance downwardly from first end 120*c*. Wall 120*a* and wings 120*b* and 120*c* bound and define a channel 120*f* that extends from first end 120*c* to second end 120*d*. Longitudinally-extending slots 120*g* are defined in each of the wings 120*b* and 120*c*. Slots 120*g* are in fluid communication with channel 120*f*. A U-shaped recess 120*h* is defined in exterior wall 120*a* extending downward from top end 120*d* towards bottom end 120*e*, terminating in an upper edge 120*a'* of wall 120*a*. Recess 120*h* is in fluid communication with channel 120*f*. Second end of spring member 126 is integrally formed with exterior wall 120*a* and extends upwardly beyond upper edge 120*a'* of upper wall 120*a*, is located outwardly from recess 120*h* and extends beyond first end 120*c* of housing 120.

Wings 120*b* and 120*c* of housing 120 are configured in a similar manner to the first finger 118*d'* and second finger 118*d"* of first spring clip 118*d* except the wings 120*b* and 120*c* are of a substantially greater height than the height of first and second fingers 118*d'*, 118*d"*. An upper region of each wing 120*b*, 120*c* terminates in a free end 124*a*, 124*b*, respectively, that extends outwardly beyond the rest of the associated wing. Wings 120*b*, 120*c* are also located and shaped as to generally longitudinally align with the first finger 118*d'* and second finger 118*d"* of first spring clip 118*d*. The free ends 124*a*, 124*b* of first wing 120*b* and second wing 120*c* may be temporarily forced apart from one another and will then return back to their original orientation relative to one another when the force is removed. First and second wings 120*b*, 120*c* effectively form a third spring clip that is aligned with the first spring clip 118*d* and second spring clip 118*e* and is capable of receiving a portion of the barrel 201 of syringe 200 or 200*a* in the portion of the channel 120*f* bounded and defined by first and second wings 120*b*, 120*c*.

Shield assembly 110 is engaged with syringe 200 or syringe 200A in a substantially identical manner to how shield assembly 10 is engaged with syringe 200 or syringe 200A. Similarly, shield assembly 110 is operable in a substantially identical manner to shield assembly 10 except that shield 16 should ideally be engaged with cradle 112 or the needle 203 of syringe 200 or 200A may be visible through recess 120*h* defined in housing 120 of carriage 120. When shield assembly 110 is engaged with the syringe 200 or 200A and the second end 120*e* of housing 120 is placed against a patient's skin and the syringe 200, 200A is moved in a direction towards the skin so that needle 203 will pierce the same, spring member 126 will become compressed, as the distance between cradle 112 and carriage 114 is reduced. When needle 203 is withdrawn from the skin and syringe 200, 200A is moved away from the skin "S", then spring member 126 will return to its original shape and location and carriage 114 will move away from cradle 112, increasing the distance therebetween.

Referring now to FIGS. 12 through 17, there is shown a third embodiment of a shield assembly in accordance with the present disclosure, generally indicate at 310. As with the first embodiment and second embodiment of the shield assembly, the third embodiment shield assembly 310 is configured to be selectively operatively engaged with a syringe such as the exemplary syringe 200 (FIG. 1-3 and FIG. 12A). The syringe 200 has been discussed earlier herein and therefore will not be described further herein for the sake of brevity.

Shield assembly 310 comprises a cradle 312, a carriage 314 (FIG. 13), and a shield 316. Cradle 312 is configured to be snap-fittingly engaged around a portion of the circumference of barrel 201 of syringe 200. Carriage 314 is configured to be operatively engaged with cradle 312 and to be movable relative thereto. When carriage 314 is moved relative to cradle 312 the carriage 314 is also thereby moved with respect to syringe 200. In particular, carriage 314 is configured to move longitudinally relative to cradle 312 and thereby to syringe 200. Shield 316 is detachably engaged with carriage 314 and thereby with cradle 312 and syringe 200. Shield 316 extends longitudinally downwardly to a sufficient degree from carriage 314 and cradle 312 so as to cover substantially the entire needle 203 (FIG. 12) extending outwardly from barrel 200 of syringe 200. Shield 316 thereby hides the needle 203 from the eyes of the child (or adult) undergoing vaccination, for example, and therefore hopefully decreases the stress and fear associated with the procedure. The various components of shield assembly 310 will now be discussed in greater detail below.

Figure 12:
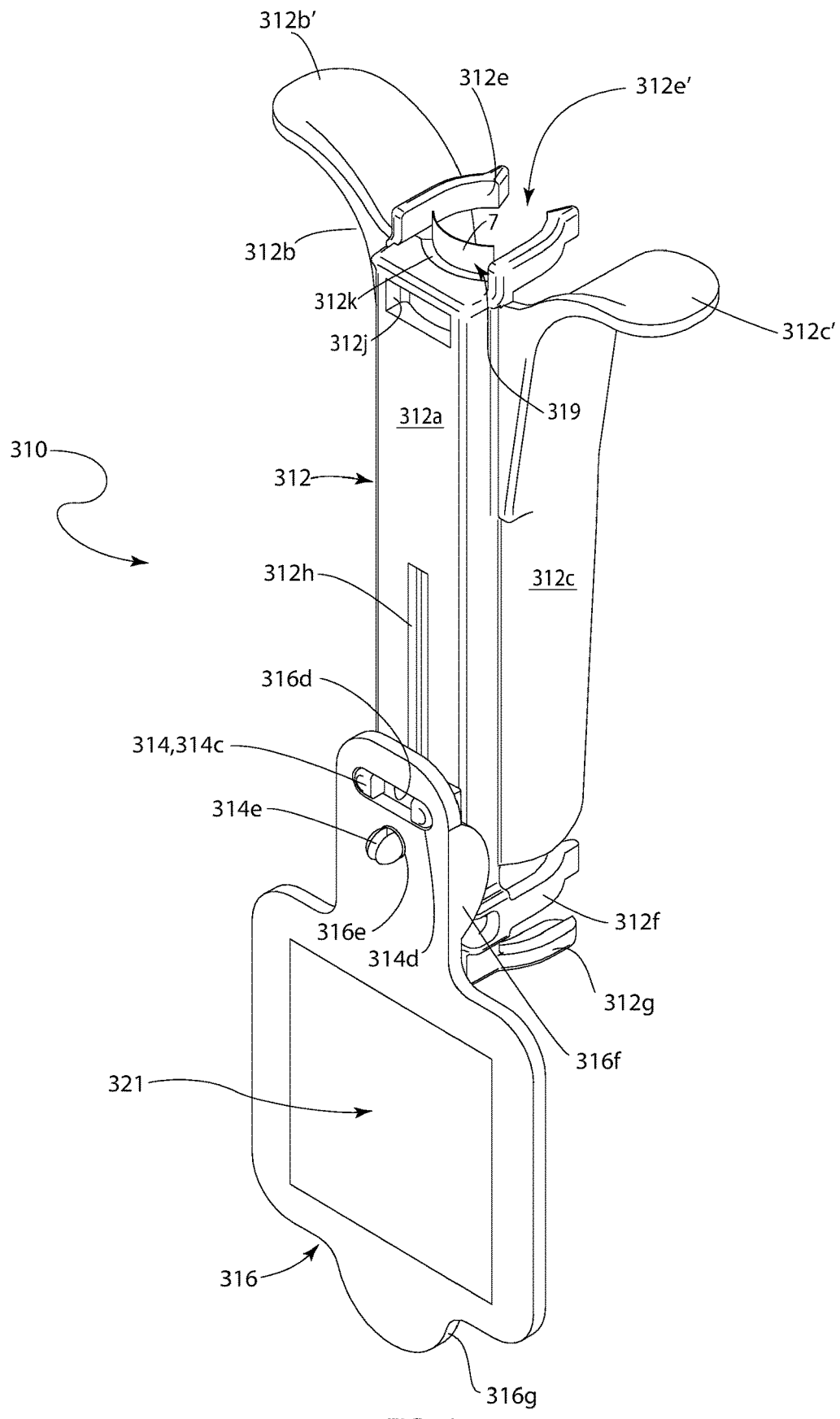
FIG. 12 is front, top perspective view of a third embodiment of a shield assembly for a syringe in accordance with the present disclosure, shown on its own.
Figure 12A:
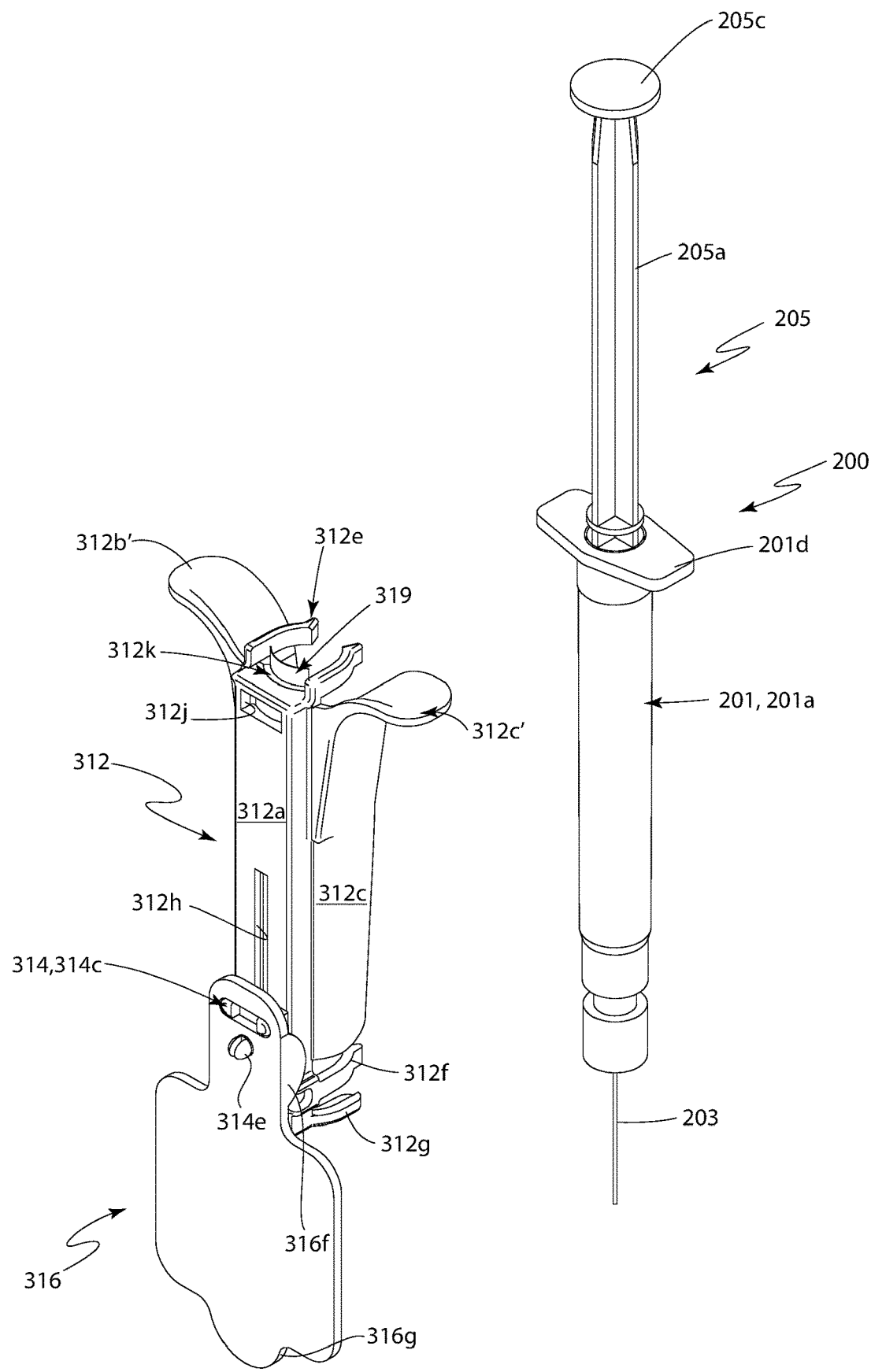
FIG. 12A is a front, top perspective view of the shield assembly of FIG. 12 shown alongside an exemplary syringe with which the shield assembly is able to be selectively engaged.
Figure 13:
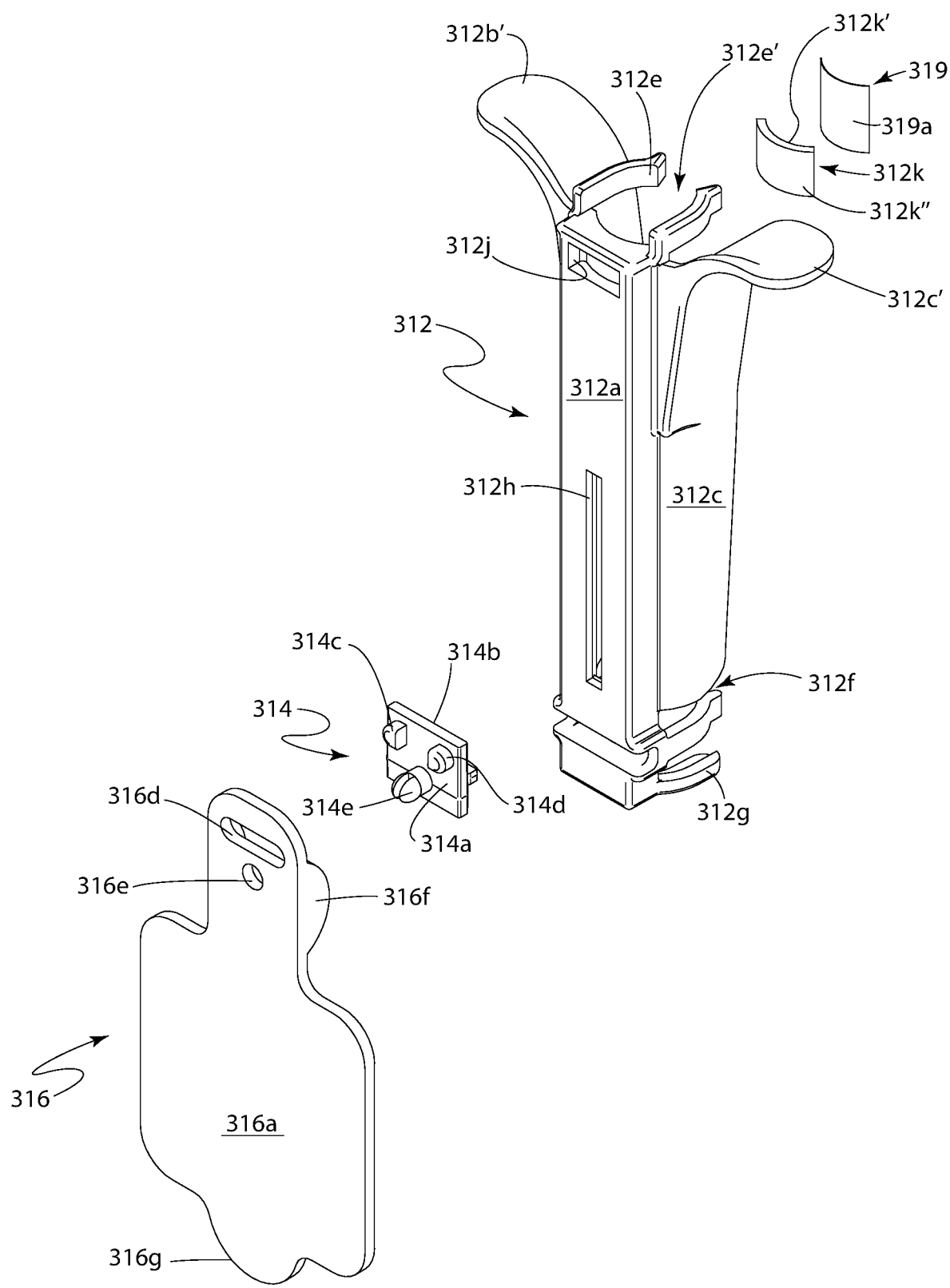
FIG. 13 is an exploded front, top perspective view of the shield assembly of FIG. 12.
Figure 14A:
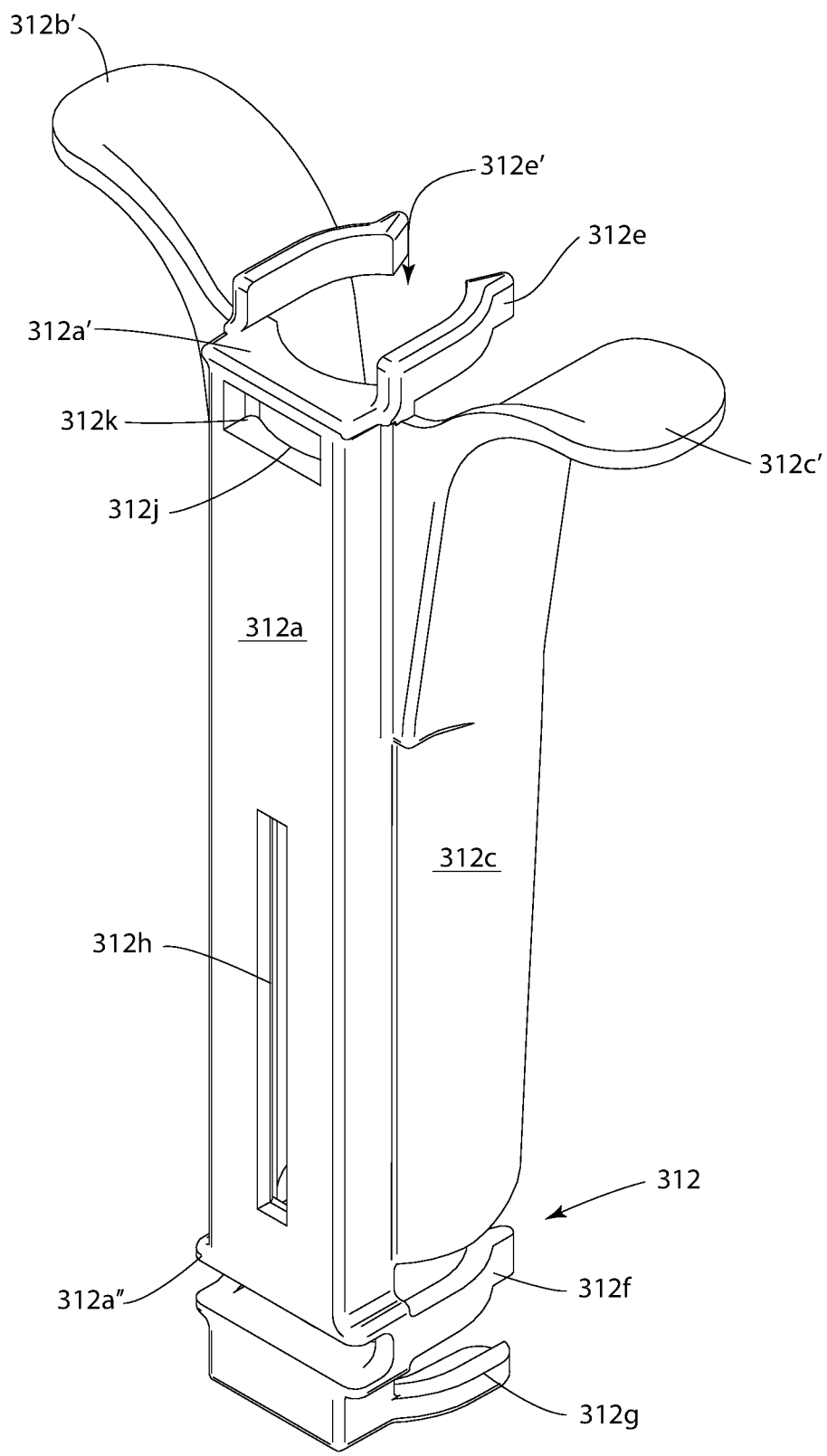
FIG. 14A is an enlarged front, top perspective view of the cradle of the shield assembly of FIG. 12 shown on its own.
Figure 14B:
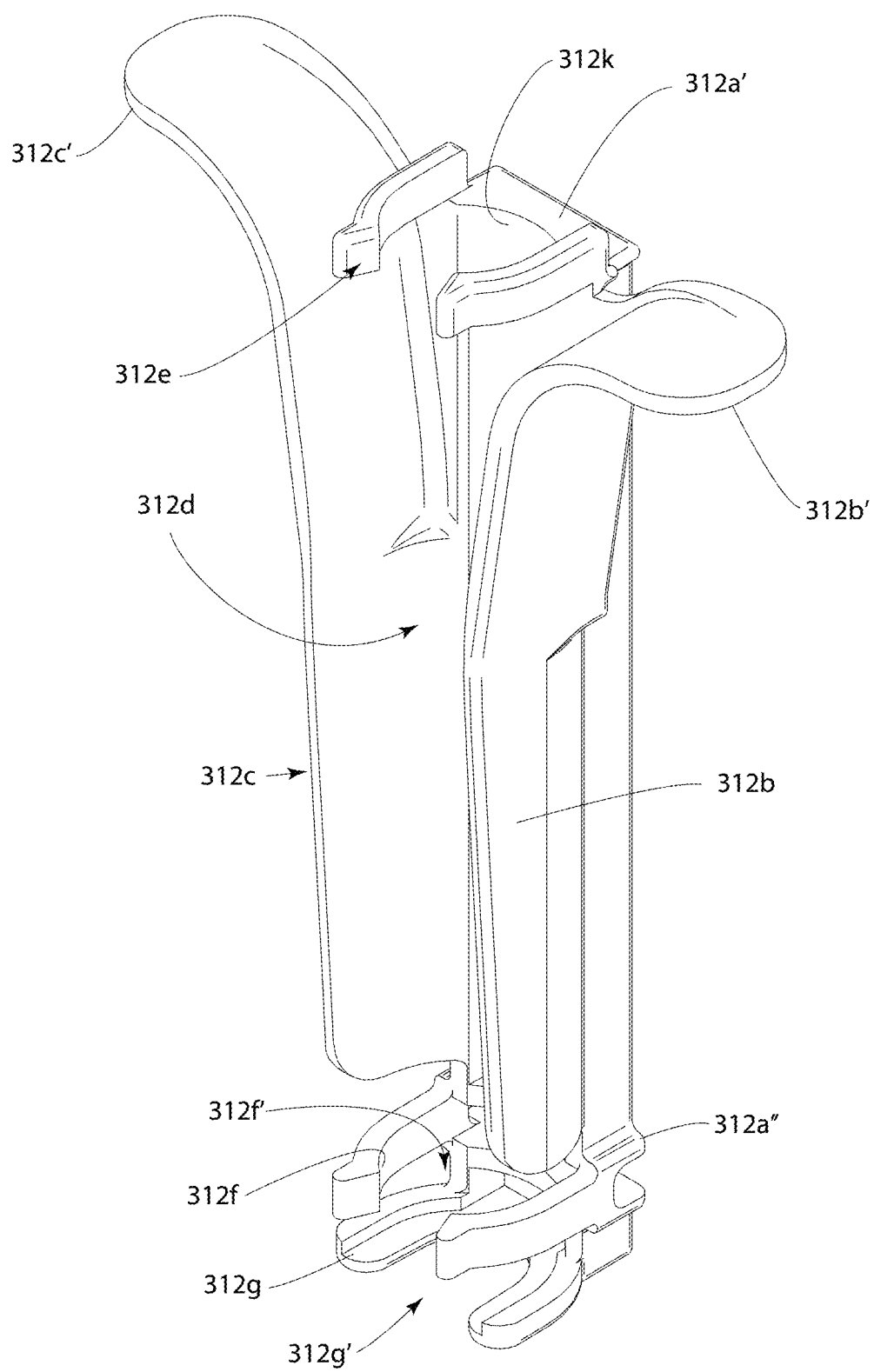
FIG. 14B is an enlarged rear, top perspective view of the cradle of the shield assembly of FIG. 12 shown on its own.

Referring now particularly to FIGS. 13, 14A and 14B, cradle 312 is described in greater detail. Cradle 312 is a substantially U-shaped component in cross-section and includes a body comprised of a front wall 312a, a left side wall 312b, and a right side wall 312c. Front wall 312a, left side wall 312b, and right side wall 312c bound and define a longitudinally-oriented channel 312d (FIG. 14B) which extends from a first end 312a' of front wall 312a to a second end 312a" thereof. Each of the left side wall 312b and right side wall 312c originate proximate second end 312a" of front wall 312a and extend upwardly beyond first end 312a' of front wall 312a. In particular, as best seen in FIGS. 14A and 14B, upper regions of each of the left side wall 312b and right side wall 312c flare outwardly away from each other in opposite directions moving away from first end 312a' of front wall 31. The flared outer regions of the left and right side walls 312b, 312c form curved "wings" 312b' and 312c' respectively. Wings 312b' and 312c' make it easier for a user to readily grasp cradle 312 and manipulate the same. The wings 312b', 312c' may also act as a stop for downward motion of the barrel flange 201d (FIG. 12A) of syringe 200, as will be discussed later herein.

In accordance with an aspect of the present disclosure, cradle 312 further include a first spring clip 312e, a second spring clip 312f, and a third spring clip 312g. Each of the spring clips 312e, 312f, 312g are substantially identical in structure and function to spring clip 18d provided on spring assembly 10 and therefore will not be described in any further detail herein other than to state that spring clip 312e extends outwardly from first end 312a' of front wall 312a and second and third spring clips 312f, 312g extend outwardly from second end 312a" of front wall 312. As is evident from FIGS. 14A and 146, second spring clip 312g is located a distance longitudinally above third spring clip 312g.

First spring clip 312e is generally U-shaped when viewed from above and includes first and second fingers (not numbered) that bracket a first aperture 312e' (FIG. 14A). The free ends of the first and second fingers may be temporarily forced apart from one another and will then return back to their original orientation relative to one another when the force is removed. FIG. 14B shows that second spring clip 312f similarly has fingers that bracket a second aperture 312f' and third spring clip 312g similar has fingers that bracket a third aperture 312g'. The first, second, and third apertures 312e', 312f', and 312g' are substantially continuous with the channel 312d defined by front wall 312a, left side wall 312b, and right side wall 312c. When cradle 312 is engaged with barrel 201 of syringe 200, the barrel 201 will be received in the aligned first aperture 312e', channel 312d, second aperture 312f', and third aperture 312g'. The fingers of the first, second, and third spring clips 312e, 312f, 312g will securely retain barrel 201 and thereby syringe 200 and cradle 312 in engagement with one another.

In accordance with an aspect of the present disclosure a longitudinally-oriented slot 312h is defined in front wall 312a of cradle 312 a short distance longitudinally upwardly from second end 312a". Slot 312h extends between an exterior surface and an interior surface of front wall 312. The purpose of slot 312h will be described further later herein.

Referring to FIG. 13, cradle 312 further includes an aperture 312j in front wall 312a in a location spaced a short distance longitudinally away from first end 312a' of front wall 312a and a distance longitudinally away from slot 312h. Aperture 312j extends between the exterior and interior surfaces of front wall 312a. A length of double-sided tape 312k may be engaged with the interior surface of front wall 312a as can best be seen in FIGS. 146, 17, and 18. Double-sided tape 312k has an inner surface 312k' and an outer surface 312k", both of which include an adhesive thereon. Double-sided tape 312k is positioned to extend across the opening to aperture 312j in front wall 312a. In particular, the outer surface 312k" of double-sided tape 312k is placed in abutting and adhering contact with the interior surface of front wall 312a. The inner surface 312k' of double-sided tape 312k bounds a region of the first aperture 312e' defined by first spring clip 312e.

A peelable layer 319 is selectively engaged with the inner surface 312k' of double-sided tape 312k to prevent tape 312k from inadvertently sticking to objects before a user wishes the tape 312k to do so. Layer 319 has an outer surface 319a (FIG. 13) which adheres to the inner surface 312k' of double-sided tape 312k. The length of peelable layer 319 is greater than the height of the double-sided tape 312k and, as a consequence, a tab of the layer 319 extends upwardly beyond first end 312a' of front wall 312a. The tab may be grasped by a user to remove peelable layer 319 from double-sided tape 312k when the user wishes to secure barrel 201 of syringe 200 within first spring clip 312e, as will be described later herein.

It will be understood that double sided tape 312k is utilized when a smaller diameter syringe 200 is to be engaged with cradle 312 and the spring clips 312e, 312f, 312g may not be able to securely hold the smaller diameter syringe 200 in cradle 312. Otherwise the double-sided tape 312k may be omitted.

Figure 15A:
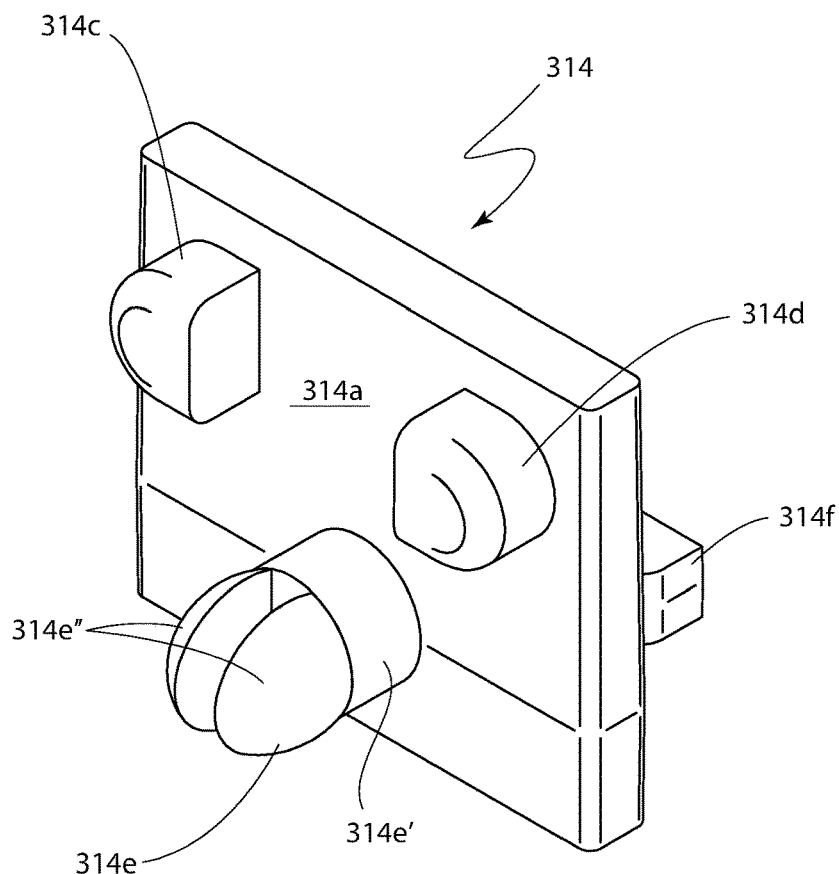
FIG. 15A is an enlarged front, top perspective view of the carriage of the shield assembly of FIG. 12 shown on its own.
Figure 15B:
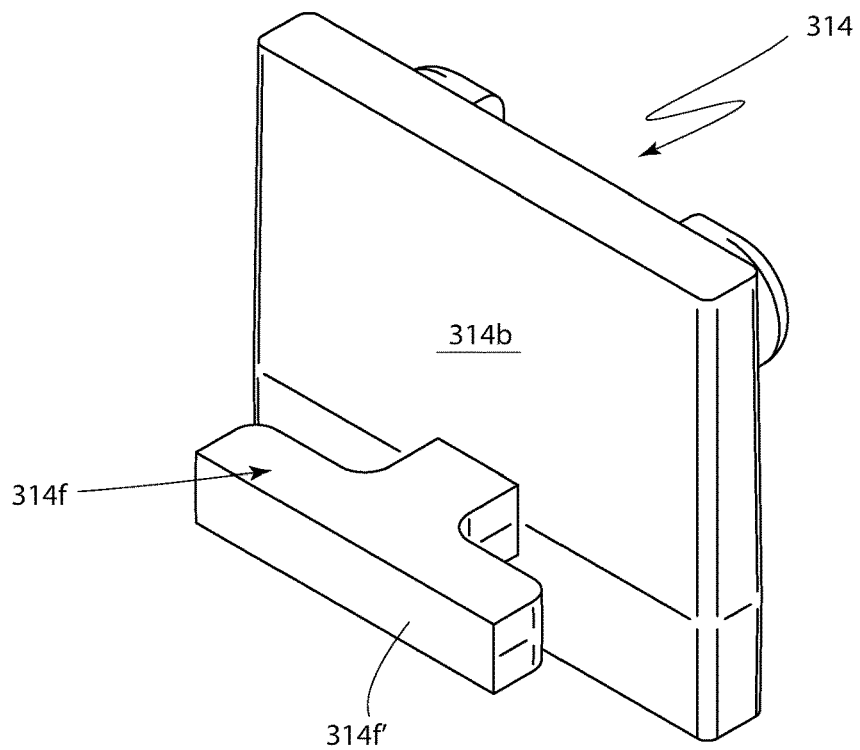
FIG. 15B is an enlarged rear, top perspective view of the carriage of the shield assembly of FIG. 12 shown on its own.

Referring to FIGS. 15A and 15B, carriage 314 is illustrated as comprising a plate that has a front surface 314a and a rear surface 314b. The plate may be of a width that is generally equivalent to a width of front wall 312a of cradle 312 (where the width of front wall 312a is the distance between left side wall 312b and right side wall 312c. A pair of laterally spaced-apart tabs 314c, 314d extend outwardly from front surface 314a. Tabs 314c, 314d are located a distance downwardly from an upper surface of the plate, as illustrated in FIG. 15A. Additionally, a button 314e extends outwardly from front surface 314a. The button 314e is located a distance upwardly from a bottom surface of the plate, is located a distance downwardly from the tabs 314c, 314d, and is generally midway between tabs 314c, 314d. Button 314e includes a shaft 314e' and a head comprised of two laterally-spaced lobes 314e". The diameter of the head of button 314e is greater than the diameter of shaft 314e' thereof. The purpose of this configuration will become evident later herein. Referring to FIG. 15B, a T-shaped projection 314f extends outwardly from rear surface 314b of the plate of carriage 314. Projection 314f is generally in the same plane as button 314e on front surface 314a.

Carriage 314 is configured to be engaged with cradle 312. In particular, the projection 314f on rear surface 314b is received through the slot 312h defined in front wall 312a of cradle 312. Projection 314f has an elongate leg 314f (FIG. 15B) which is of a thickness suitable to be received through the slot 312h in front wall 312a of cradle 312. The engagement between carriage 314 and cradle 312 is accomplished by positioning the rear surface 314b of the plate of carriage 314 proximate front wall 312a of cradle 312. The plate is oriented in such a way as to align the leg 314f with the slot 312. The plate is then pushed towards front wall 312a of cradle 312 so that the leg 312f' of projection 312 moves through the slot 312h. When the leg 314f of projection 314f clears the interior surface of the front wall 312a, the plate is rotate through 90° to secure carriage 314 to cradle 312. In particular, the plate of carriage 314 is rotated so that the button 314e on front surface 314a is located closer to second side 314a" of front wall 314a than are the two tabs 314c, 314d. When carriage 314 is so engaged with cradle 312, carriage 314 is able to slide longitudinally along slot 312h. The purpose of carriage 314 and its engagement with cradle 312 will be described further later herein.

Figure 16A:
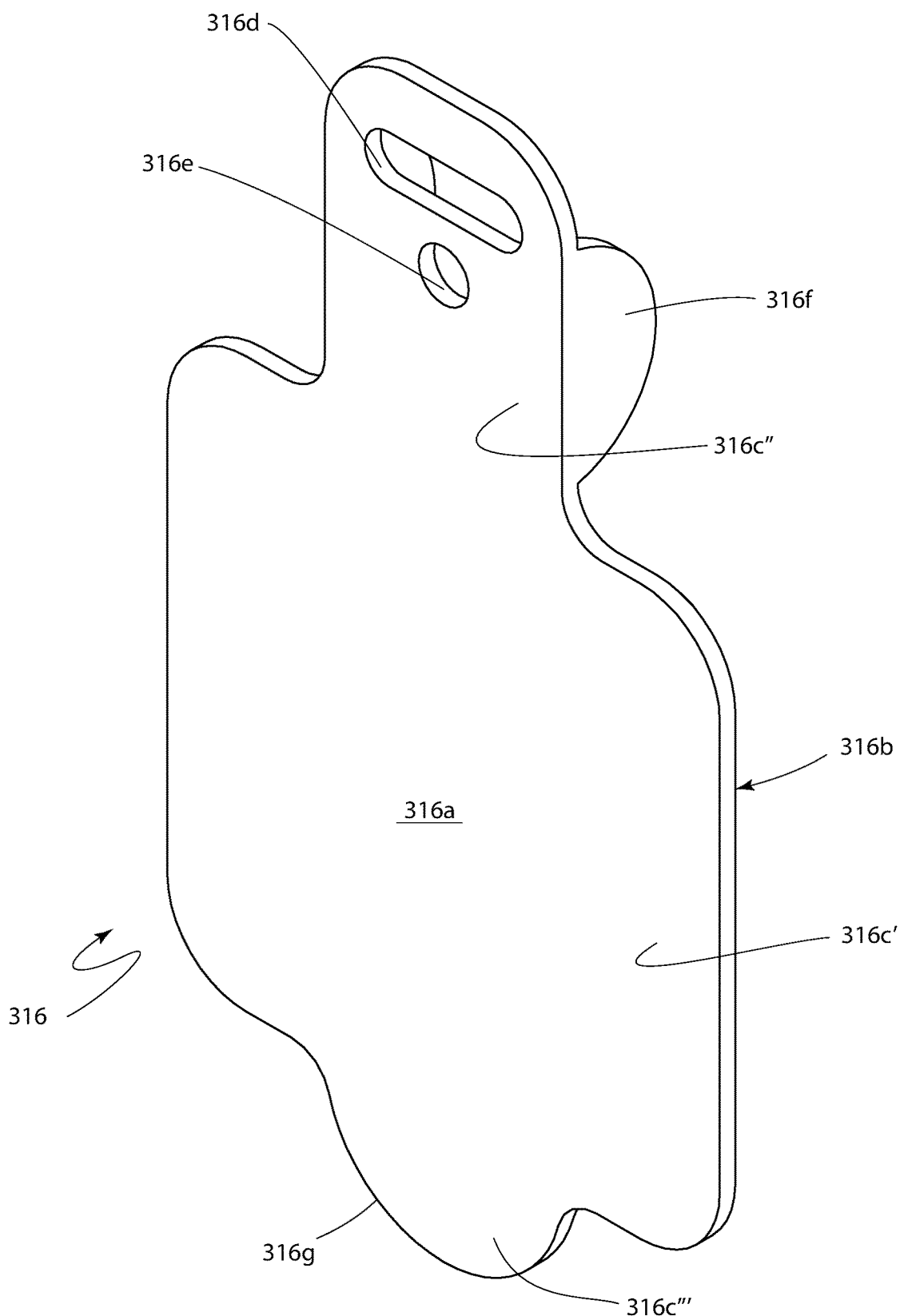
FIG. 16A is an enlarged front, top perspective view of the shield of the shield assembly of FIG. 12 shown on its own.
Figure 16B:
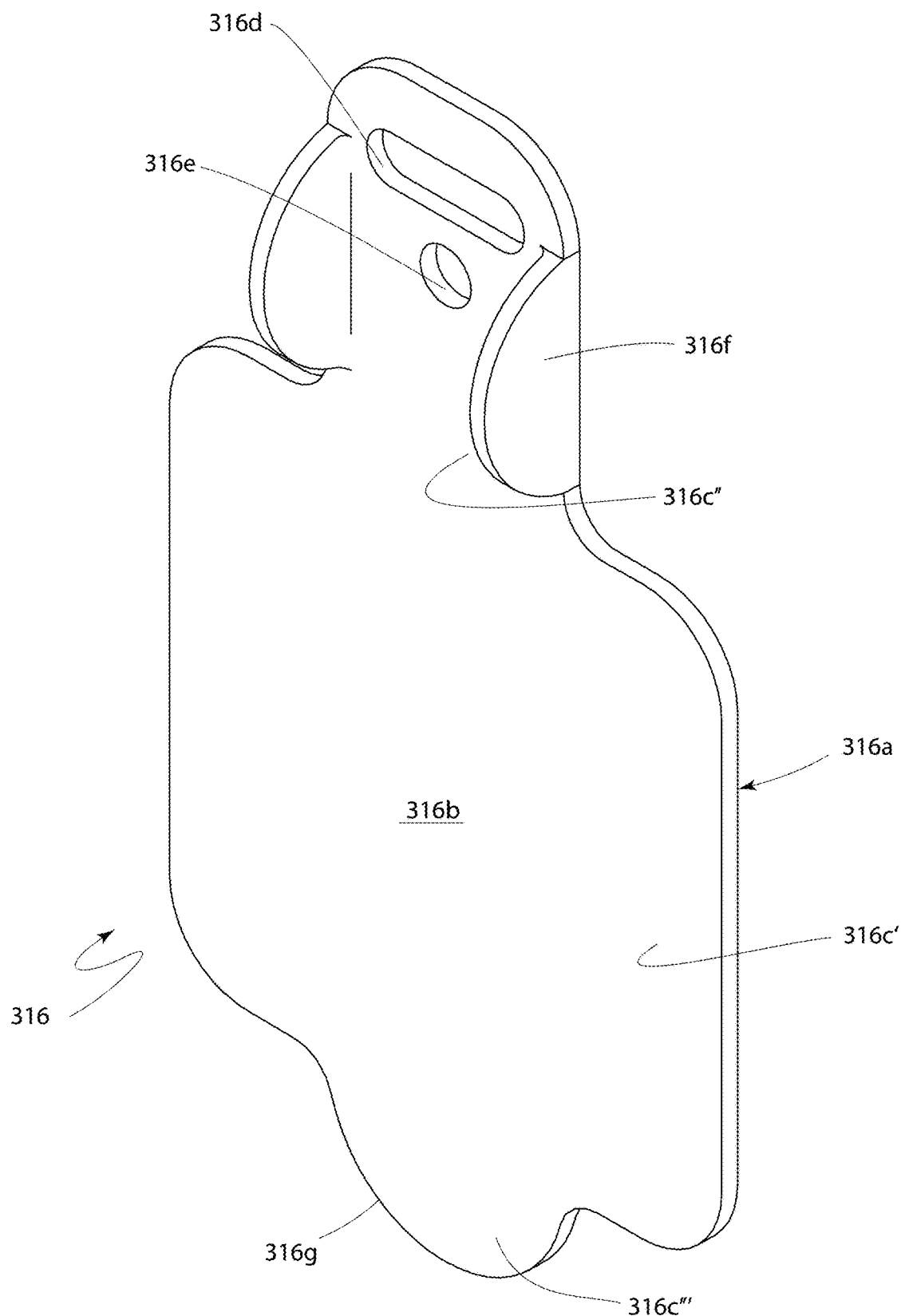
FIG. 16B is an enlarged rear, top perspective view of the shield of the shield assembly of FIG. 12 shown on its own.

Referring now to FIGS. 16A and 16B shield 16 is shown in isolation. Shield 16 is a generally flat plate having a front surface 16a and a rear surface 16b. Shield 16 when viewed from the front may be of any desired shape. As illustrated in the present embodiment, shield 16 includes a generally square central region 316c', a generally rectangular first region 316v" extend outwardly from the central region 316v' in a first direction, and a generally semi-circular third region 316c'" extending outwardly from the central region 316c' in a second direction. The first region 316c" and second region 316c'" are of a smaller width than the central region 316c'. It will be understood that this configuration is exemplary only any other desired configurations of shield 316 may be utilized instead.

A slot 316d and an aperture 316e are defined in first region 316c" of shield 316. Both slot 316d and aperture 316e extend from the front surface 316a through to the rear surface 316b of shield 316. Slot 316d is positioned a distance downwardly from a first end of shield 316 and aperture 316e is positioned a distance below slot 316d. Slot 316d is configured to receive tabs 314c and 314d of carriage 314 therethrough and aperture 316e is configured to receive button 314e of carriage 314 therethrough when shield 316 is engaged with carriage 314, as will be discussed later herein.

Referring still to FIGS. 16A and 16B, first region 316c' of shield 316 is provided with a pair of flanges 316f that extend rearwardly for a distance beyond rear surface 316b. The distance between flanges 316f is such that the plate of carriage 314 will fit therebetween when shield 316 is engaged with carriage 314. In one aspect, the distance between flanges 316f is generally equal to the width of the plate of carriage 314 such that when shield 316 engages carriage 314 there is a friction fit between the flanges 316f and the carriage's plate. As indicated earlier herein, second region 316c'" of shield is semi-circular in shape. In particular, the outermost edge 316g of second region 316c'" is curved. This rounded edge 316g is provided so that when syringe 200 is to be used, the shield 316 will rest comfortably upon the patient's skin.

In accordance with an aspect of the present disclosure, a sticker 21 (FIG. 1) with an aesthetically pleasing design thereon may be applied to front surface 316a of shield 316. In particular, the design may be pleasing to young children in order to act as a distraction from the injection procedure. The sticker 21 may be of a type that is permanently adhered to front surface 316a or the sticker 21 may be of a type that is selectively removable from front surface 316a.

Figure 17:
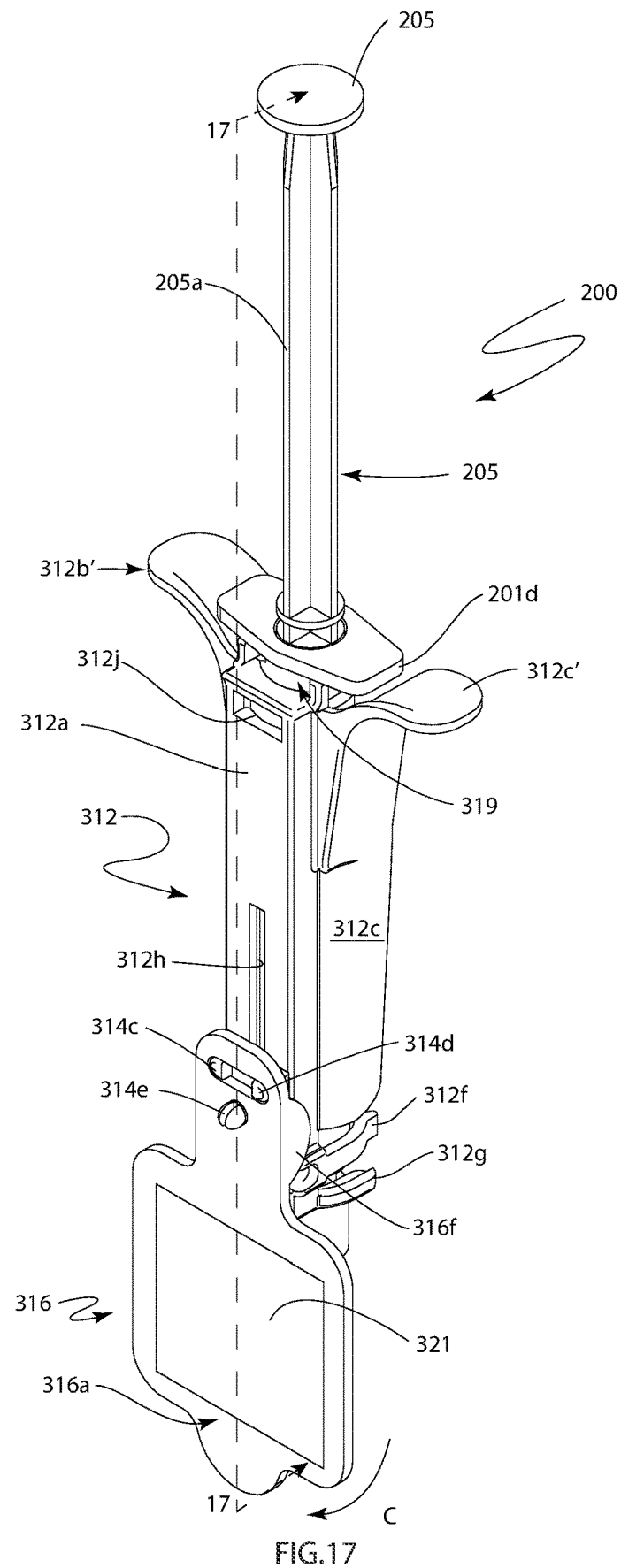
FIG. 17 is a front, top perspective view of the shield assembly of FIG. 12 shown engaged with the exemplary syringe and showing the syringe in a first position prior to use thereof.

Referring now to FIG. 17, shield assembly 310 is assembled for use by engaging carriage 314 to cradle 312 as described earlier herein, and then engaging shield 316 with carriage 314. Shield 316 is engaged with carriage by positioning rear surface 316b of shield 316 in proximity to front surface 314a of the plate of carriage 314. The shield 316 is positioned particularly such that slot 316d aligns with the tabs 314c, 314d on carriage 314, and the aperture 316d aligns with button 314e on carriage 314. It should be noted that slot 316d is of a length that is marginally greater than the distance between the outermost side surfaces of the tabs 314c and 314d. Additionally, tabs 314c, 314d are sized so that they may be received through slot 316d of shield 316. Additionally, the height of slot 316d in shield 316 is marginally greater than the height of tabs 314c, 314d. Similarly, aperture 316e defined in shield 316 is marginally greater than the diameter of button 314e provided on carriage 314. This configuration helps to ensure that when shield 316 is engaged with carriage 314, there is a friction fit between shield 316 and carriage 314. In one aspect, the shield 316 may snap-fittingly engage carriage 314. Furthermore, when button 314e is received through aperture 316e, lobes 314e" of button 314e initially flex inwardly towards one another but then return to their original positions once the head of button 314e clears front surface 316a of shield 316. This arrangement helps ensure that shield 316 is retained in engagement with carriage 314 and will not accidentally dislodge from carriage 314 when shield assembly 316 is used. Furthermore, flanges 316f on shield 316 abut the side surfaces of the plate of carriage 314. This abutting engagement helps guard against rotation of shield 316 relative to carriage 314 when shield assembly 310 is used.

Figure 18:
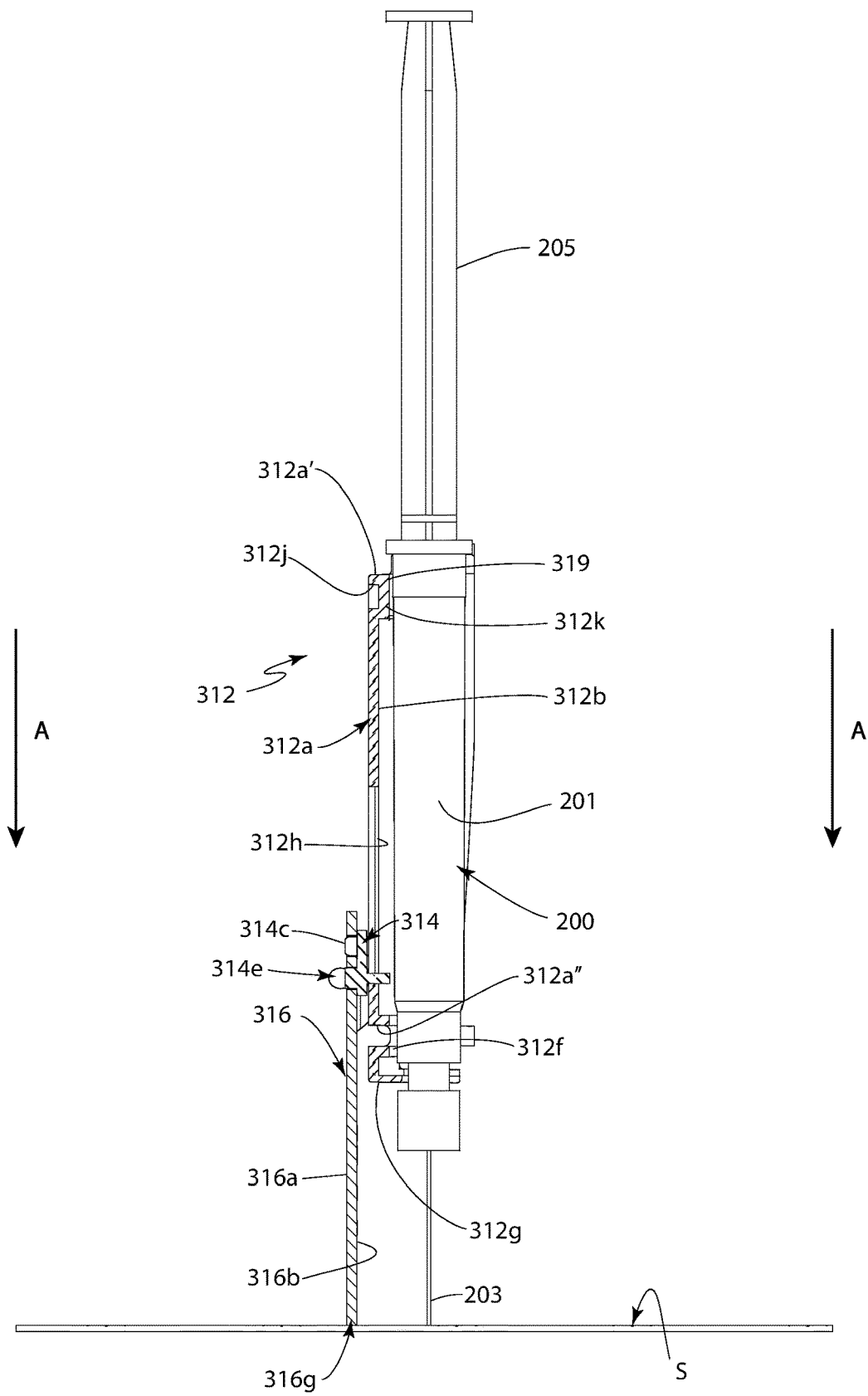
FIG. 18 is a longitudinal cross-section of the shield assembly shown engaged with the syringe and taken along line 18-18 of FIG. 17.
Figure 19:
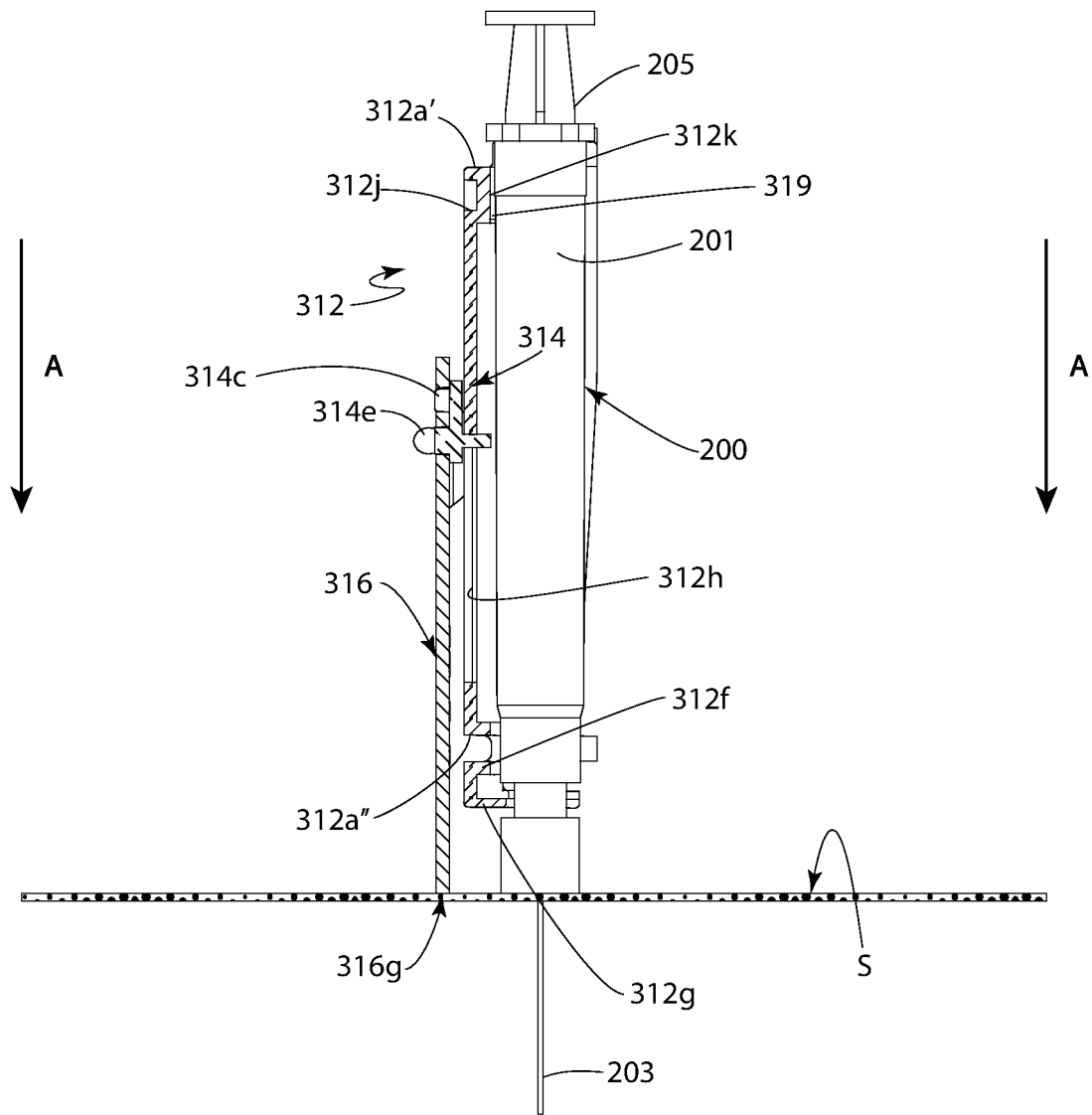
FIG. 19 is a longitudinal cross-section of the shield assembly and syringe similar to FIG. 18 but with the syringe in a second position during use with the plunger depressed and delivering a dose of medicine or vaccine into a patient's body.

Referring now to FIGS. 12A, 18 and 19, shield assembly 310 is used in the following manner to perform an injection procedure. (It will be understood that in other instances, shield assembly 310 may be engaged with syringe 200 if a bodily fluids withdrawal procedure is to be undertaken, e.g., drawing blood.). In a first step, shield assembly 310 is engaged with syringe 200. In particular, shield assembly 310 is positioned such that the outermost ends of the fingers of the first, second and third spring clips 312e, 312f, and 312g are located proximate barrel 201 of syringe 200. Shield assembly 310 is then moved towards syringe barrel 201 such that the fingers of the three spring clips spread apart and barrel 201 is received into the aligned openings 312e', 312d, 312f and 312g. At this point, syringe 200 and shield assembly 316 are operatively engaged with one another. It should be noted that when shield assembly 316 is engaged with syringe 200 the barrel 201 and needle 203 extending from the barrel 201 are hidden from view by shield assembly 316.

The syringe 200 with engaged shield assembly 316 is then grasped in the fingers of the health care professional using the wings 312b' and 312c' to assist. The health care professional will then hold and position the device in an appropriate location on a patient's skin "S" in order to inject the contents of the syringe 200 into the patient's body. In particular, the curved edge 316g of shield 316 is placed on the patients skin "S" and slight downward pressure, in the direction indicated by arrow "A" is applied to the syringe 200 to bring the tip of needle 203 into contact with the skin "S". The downward pressure may cause carriage 314 on shield assembly 310 to slide slightly upwardly along slot 312h of cradle 312, in an opposite direction to arrow "A".

When the tip of needle 203 and shield 316 are in contact with the skin "S" downward pressure is applied to syringe 200 in the direction of arrow "A", thereby causing needle 203 to pierce the skin "S" (FIG. 19) and moving barrel 201 closer to the skin "S". During this downward motion, cradle 312 of shield assembly 310 moves with barrel 201 of syringe 200 and shield 316 of shield assembly 310 stays in abutting contact with the skin "S". Carriage 314 slides upwardly along slot 312h of cradle 312 to enable the relative motion between cradle 312 and shield 316. At the appropriate time, the health care professional will depress the plunger 205 on syringe 200, as indicated by arrow "B", in order to deliver the contents of syringe 200 into the patient's body. When the contents of syringe 200 are delivered, the needle 203 is withdrawn from the patient's body. During insertion, injection, and withdrawal, the barrel 201 and needle 203 of syringe remain hidden from the patient's view by shield assembly 310.

In some instances, such as when a sticker has been applied to shield 316, the shield 316 itself may be disengaged from shield assembly 310 and be given to a young child as a "reward" for having an injection. Shield 316 may be disengaged from carriage 314 by grasping second region 316c" of shield are rotating the bottom end of shield 316 in the direction of arrow "C" (FIG. 17). This rotational motion causes the button 314e to move back through aperture 316e on shield 316, thereby breaking the frictional engagement between the two components. In other instances, where the sticker is of a removable type, the sticker may be peeled free from front surface 316a of shield 316 and given to the child as the "reward".

In some instances, shield assembly 310 is reusable. In this instance, after the injection procedure (or bodily fluids withdrawal procedure) is over, syringe 200 is disengaged from shield assembly 310, a new shield 316 is engaged with carriage 314 (if the previous shield 316 was removed), and then a new syringe 200 may be operatively engaged with shield assembly 310, readying the combined device for the next patient. If only the sticker was removed from shield 316, a new sticker may be applied thereto.

In other instances, the shield assembly 310 is a single use device that is discarded after a single injection procedure or bodily fluids withdrawal procedure.

In summary, a method of using any of the embodiments of shield assembly 10, 110, 310 to reduce stress in a patient receiving medical treatment, particularly a young child, comprises engaging a cradle, such as cradle 312 of a shield assembly, such as shield assembly 310 with a syringe 200. The method further includes extending a shield, such as shield 316 of the shield assembly over a needle 203 extending outwardly from a barrel 201 of the syringe 200; placing an edge, such as edge 316g of the shield against the patient's skin "S"; piercing the patient's skin with a tip of the needle 203; manipulating a plunger 205 extending from the syringe's barrel 201 to perform one of injecting a substance into the patient's body and withdrawing fluid from the patient's body; and withdrawing the needle 203 from the patient's skin "S".

The method may further comprise hiding the needle 203 from the patient's view with the shield 316 prior to piercing the patient's skin "S" and up to after withdrawing the needle 203 from the patient's skin "S". The method further comprises providing a child-pleasing image on the shield. In one embodiment, the child-pleasing image is provided on the shield by applying a sticker 321 (FIG. 12) on a front face of the shield. In other embodiments, the shield itself may be molded or otherwise formed into a child-pleasing image or shape, such as is illustrated by shield 16 in FIG. 1.

Engaging the cradle, such as cradle 312 with the syringe 200 includes snap-fitting one or more spring clips 312e, 312f, and 312g provided on the cradle 312 around a portion of a circumference of the barrel 201 of the syringe 200. Engaging the shield, such as shield 316 with the cradle, such as cradle 312 may include engaging a movable carriage, such as carriage 314, with the cradle 312 and mounting the shield 316 on the movable carriage 314. The method further comprises defining a slot, such as slot 312h, in the cradle 312; extending a projection, such as projection 314f, on the carriage 314 through the slot 312h defined in the cradle 312; and sliding the projection 314f and thereby the carriage 314 along the slot 312h. The shield 316 may be detachably engaged with the cradle 316. In one embodiment, the shield 316 is detachably engageable with the cradle via detachably engaging the shield 316 to the carriage 314 and detachably engaging the carriage 314 with the cradle 312.

In one embodiment, instead of carriage 314 and shield 316 being separate components, the carriage and the shield may be integrally formed with one another. For example, in the integrally formed carriage and shield, the slot 316d and aperture 316e of shield 316 may be omitted along with the tabs 314c, 314d, and button 314e of carriage 314. The front surface 314a of carriage 314 may, instead, be integrally formed with the rear surface 316b of shield 316 such that a spacer block extends rearwardly from the rear surface 316b of shield 316. The projection 314f may then be provided on a rear surface of the spacer block of the integrally formed shield and carriage. The integrally-formed component will then be engageable with cradle 312 in a manner similar to how carriage 314 is described earlier herein as being engaged with cradle 312.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," "an exemplary embodiment," or "other embodiments," or the like, means that a particular feature, structure, or characteristic described in connection with the embodiments is included in at least some embodiments, but not necessarily all embodiments, of the invention.

The various appearances "an embodiment," "one embodiment," "some embodiments," "one particular embodiment," "an exemplary embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, the method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. A shield assembly for a syringe comprising:
   a cradle configured to operatively engage a portion of the syringe;
   a shield movably engaged with the cradle, said shield being adapted to cover a needle extending outwardly from a barrel of the syringe;
   a carriage operative to movably engage the shield to the cradle;
   wherein the shield is selectively movable relative to the cradle during use of the syringe; and
   wherein the carriage is movably engaged with the cradle.

2. The shield assembly according to claim 1, further comprising:
   a slot defined in the cradle;
   a projection provided on the carriage, said projection sized to be received through the slot; wherein the projection and thereby the carriage is selectively slidable along the slot.

3. The shield assembly according to claim 1, wherein the shield is detachably engaged with the carriage.

4. The shield assembly according to claim 1, further comprising an aesthetically pleasing image provided on the shield.

5. The shield assembly according to claim 4, wherein the aesthetically pleasing image on the shield comprises a sticker applied to the shield.

6. The shield assembly according to claim 4, wherein the shield is three-dimensionally formed into the aesthetically pleasing image.

7. The shield assembly according to claim 1, further comprising one or more spring clips provided on the cradle, said one or more spring clips being adapted to engage a portion of a circumference of the barrel of the syringe.

8. The shield assembly according to claim 1, further comprising a rounded bottom edge provided on the shield, wherein the rounded bottom edge is adapted to contact skin of a patient during use of the syringe.

9. The shield assembly according to claim 1, further comprising a coil spring interposed between the carriage and the cradle.

10. In combination:
    a syringe having a barrel defining a bore therein which is adapted to receive a volume of liquid therein, and a plunger that is movable through the bore; and
    a shield assembly comprising:
       a cradle that is detachably operatively engageable about a portion of an exterior circumference of the barrel; and
       a shield movably engaged with the cradle and configured to move relative to the cradle during use of the syringe;
    wherein the shield substantially continuously obscures a needle extending outwardly from one end of the barrel of the syringe during operation of the syringe.

11. A shield assembly for a syringe comprising:
    a cradle configured to operatively engage a portion of the syringe;
    a shield movably engaged with the cradle, said shield being adapted to cover a needle extending outwardly from a barrel of the syringe;
    a carriage operative to movably engage the shield to the cradle;
    a coil spring interposed between the carriage and the cradle; and
    wherein the shield is selectively movable relative to the cradle during use of the syringe.

* * * * *